US012558247B2

(12) United States Patent
Hawkins

(10) Patent No.: US 12,558,247 B2
(45) Date of Patent: Feb. 24, 2026

(54) ORTHOPEDIC DEVICE

(71) Applicant: Michael Hawkins, Coeur d'Alene, ID (US)

(72) Inventor: Michael Hawkins, Coeur d'Alene, ID (US)

( * ) Notice: Subject to any disclaimer, the term of this patent is extended or adjusted under 35 U.S.C. 154(b) by 338 days.

(21) Appl. No.: 17/229,850

(22) Filed: Apr. 13, 2021

(65) Prior Publication Data

US 2021/0315723 A1      Oct. 14, 2021

Related U.S. Application Data

(60) Provisional application No. 63/009,109, filed on Apr. 13, 2020.

(51) Int. Cl.
A61F 5/00 (2006.01)
A61F 5/02 (2006.01)

(52) U.S. Cl.
CPC .................................... A61F 5/024 (2013.01)

(58) Field of Classification Search
CPC .. A61F 5/02; A61F 5/022; A61F 5/024; A61F 5/026; A61F 5/028; A61F 5/03; A61F 5/04; A61F 5/042; A61F 5/048; A61F 5/05; A61F 5/05825; A61F 5/05841; A61F 5/05883; A61F 5/0585; A61F 5/05858; A61F 5/24; A61F 5/30; A61F 5/32; A61F 5/37; A61F 5/3715; A61F 5/3723; A61F 5/373; A61G 13/12; A61G 13/121; A61G 13/122; A61G 13/1225; A61G 13/123; A61G 13/1235; A61G 13/124; A61G 13/1245; A61G 13/125; A61G 13/1255; A61G 7/1084; A61G 7/1086; A61G 7/1088; A61G 7/109; A61G 7/1092; A61G 7/1094; A61G 7/1096; A61B 5/4561–4595
USPC ........................................................... 602/19
See application file for complete search history.

(56) References Cited

U.S. PATENT DOCUMENTS

| | | | | |
|---|---|---|---|---|
| 1,092,737 A * | 4/1914 | Mennis | ..................... | A41H 1/02 |
| | | | | 33/8 |
| 2,818,648 A * | 1/1958 | Jochheim | ................. | A41H 1/04 |
| | | | | 33/8 |
| 3,353,532 A * | 11/1967 | Ellis | ..................... | A61H 1/0218 |
| | | | | 606/241 |
| 3,955,285 A * | 5/1976 | Moeckl | .................. | G01B 5/207 |
| | | | | 33/515 |
| 5,092,592 A * | 3/1992 | FitzMaurice | .......... | A63B 69/38 |
| | | | | 473/464 |
| 5,121,753 A * | 6/1992 | Paez | ...................... | A61B 5/103 |
| | | | | 600/587 |
| 7,291,097 B1 * | 11/2007 | Dace | ..................... | A61H 3/008 |
| | | | | 482/69 |

(Continued)

*Primary Examiner* — Adam Baker

(57) ABSTRACT

An orthopedic device comprises a frame assembly comprising a parallel frame member and a perpendicular frame member. Each of the parallel frame member and the perpendicular frame member are substantially elongate in shape, and each have a first end and a second end. The orthopedic device further comprises at least three primary extensions each having a mount end and a free end. The perpendicular frame member is coupled by the first end thereof to the parallel frame member along the length of the parallel frame member between the first end and the second end thereof. Each of the at least three primary extensions is adjustably disposed by the mount end thereof along the frame assembly.

16 Claims, 18 Drawing Sheets

(56) References Cited

U.S. PATENT DOCUMENTS

| 9,352,675 | B2 * | 5/2016 | Walker | .................... | B60N 2/85 |
| 2005/0203453 | A1 * | 9/2005 | Willner | .................. | A61F 5/024 |
| | | | | | 602/19 |
| 2009/0307845 | A1 * | 12/2009 | Rao | .................... | A61G 13/0072 |
| | | | | | 5/624 |

* cited by examiner

ORTHOPEDIC DEVICE

CROSS REFERENCE TO RELATED APPLICATIONS

This application claims the benefit of U.S. Provisional Patent Application No. 63/009,109, filed 2020 Apr. 13 by the present inventor, which is hereby incorporated by reference herein in its entirety.

FIELD OF THE INVENTION

The invention relates to an orthopedic device.

FEDERALLY SPONSORED RESEARCH

None

SEQUENCE LISTING

None

BACKGROUND

When a skeletally immature patient is diagnosed with a orthopedic deformity such as scoliosis or hyperkyphosis a custom made brace is often prescribed for the patient during the ages of skeletal immaturity. Throughout history doctors, orthotists, and other medical practitioners (brace makers) have employed various techniques for casting patients' body shapes and measuring patients' body dimensions in order to fabricate custom spinal orthoses. The techniques used in modern practice include casting a patient's torso with a physical material such as a combination of plaster & gauze that is formable when wet, and hardens quickly creating a rigid form with which a mold can be made; or, using a digital 3-dimensional optical scanner to record the dimensions and shape of the patient's torso which is rendered as a 3-dimensional shape on a computer screen.

Brace makers may fabricate spinal orthoses based on a patient's torso shape that is casted in a relaxed, uncorrected position or in a pre-aligned position that is corrected to the best of the brace maker's ability. Brace makers who cast patients in a pre-aligned/corrected position have used a variety of methods in an attempt to achieve the most corrected position in which the patient's spine is closest to that of a physiologically normal spine. The methods include: utilizing stationary fixtures such as a horizontal bar that patients bend over or lean against; stationary frames (anchored to the floor, or walls) with extensions to push and apply external force to the patient's body; and, utilizing the brace maker's own hands, arms and body to hold the patient in a corrected position.

After casting the shape and dimension of a patient's torso using one of the previously described techniques, the brace maker may make modifications to the shape of the cast or mold to optimize the fit and effectiveness of the brace once it is fabricated. Modifying the shape of the cast or mold in an attempt to improve the positioning of the patient's spine in the finalized brace is a subjective process requiring guesswork on the part of the bracemaker and is susceptible to error. Generally, casting a patient in the uncorrected position requires more modification of the shape of the cast or mold to achieve the desired position and alignment of the patient's spine in the final fabricated spinal orthosis.

Bracemakers have attempted to improve the process by casting patients in a corrected position as previously described, however casting the patient in a position in which a brace is capable of holding a patient has been difficult. Some bracemakers attempt to utilize a frame or other object that is completely stabilized (i.e. fixed to the floor or wall or weighs so much that it is essentially fixed to the floor) to manipulate the patient's torso & spine position. A spinal orthosis is not capable of manipulating the patient's torso & spine position in such a manner, so inherently, the cast of the patient's torso being manipulated by a stable device is not a realistic impression of the effect of a proposed spinal orthosis. A spinal orthosis, when worn by a patient, is held in place by the features and characteristics of the patient's own body. Therefore, any method of positioning a patient's torso and spine for casting that involves the use of a stabilized or fixed device will only provide an unrealistic estimate of the effect of a potential spinal orthosis.

Skeletally immature patients diagnosed with a orthopedic deformity such as scoliosis may alternatively be treated with a cast around their torso purposed to hold the patient in a position of improved spinal alignment. The traditional method for applying the cast involves using a combination of traction and the practitioner's hands to manually improve the patient's spinal position with the unhardened cast material applied to the patient. The practitioner continues to manually hold the position of the patients torso while the cast material is hardening until it is completely hardened. This is an imprecise method that requires using a practitioner's hands and arms over a prolonged period that is subject to an even greater amount of error as the practitioner's upper extremities become fatigued.

Skeletally immature patients diagnosed with a orthopedic deformity such as scoliosis or hyperkyphosis may alternatively be prescribed specific physical therapy exercises that require the patient to move the position of their torso assymetrically based on the cues and instructions of the physical therapist. The physical therapist may use facilitory or inhibitory techniques to assist the patient in performing the desired movement. The patient's, in some cases, experience a great amount of difficulty in initially learning how to achieve the desired movement. It can be difficult for a physical therapist to guide a patient experiencing difficulty achieving the desired movement as it can require three or more points of contact with the patient in order to guide the patient into achieving the desired movement.

SUMMARY

An orthopedic device comprises a frame assembly comprising a parallel frame member and a perpendicular frame member. Each of the parallel frame member and the perpendicular frame member are substantially elongate in shape, and each have a first end and a second end. The orthopedic device further comprises at least three primary extensions each having a mount end and a free end. The perpendicular frame member is coupled by the first end thereof to the parallel frame member along the length of the parallel frame member between the first end and the second end thereof. Each of the at least three primary extensions is adjustably disposed by the mount end thereof along the frame assembly.

BRIEF DESCRIPTION OF THE DRAWINGS

In order that the features, aspects, and advantages of an orthopedic device may be more readily understood, reference will now be made to the accompanying drawings which illustrate embodiments of the orthopedic device.

DETAILED DESCRIPTION OF VARIOUS EMBODIMENTS

Advantages

Figure 1:
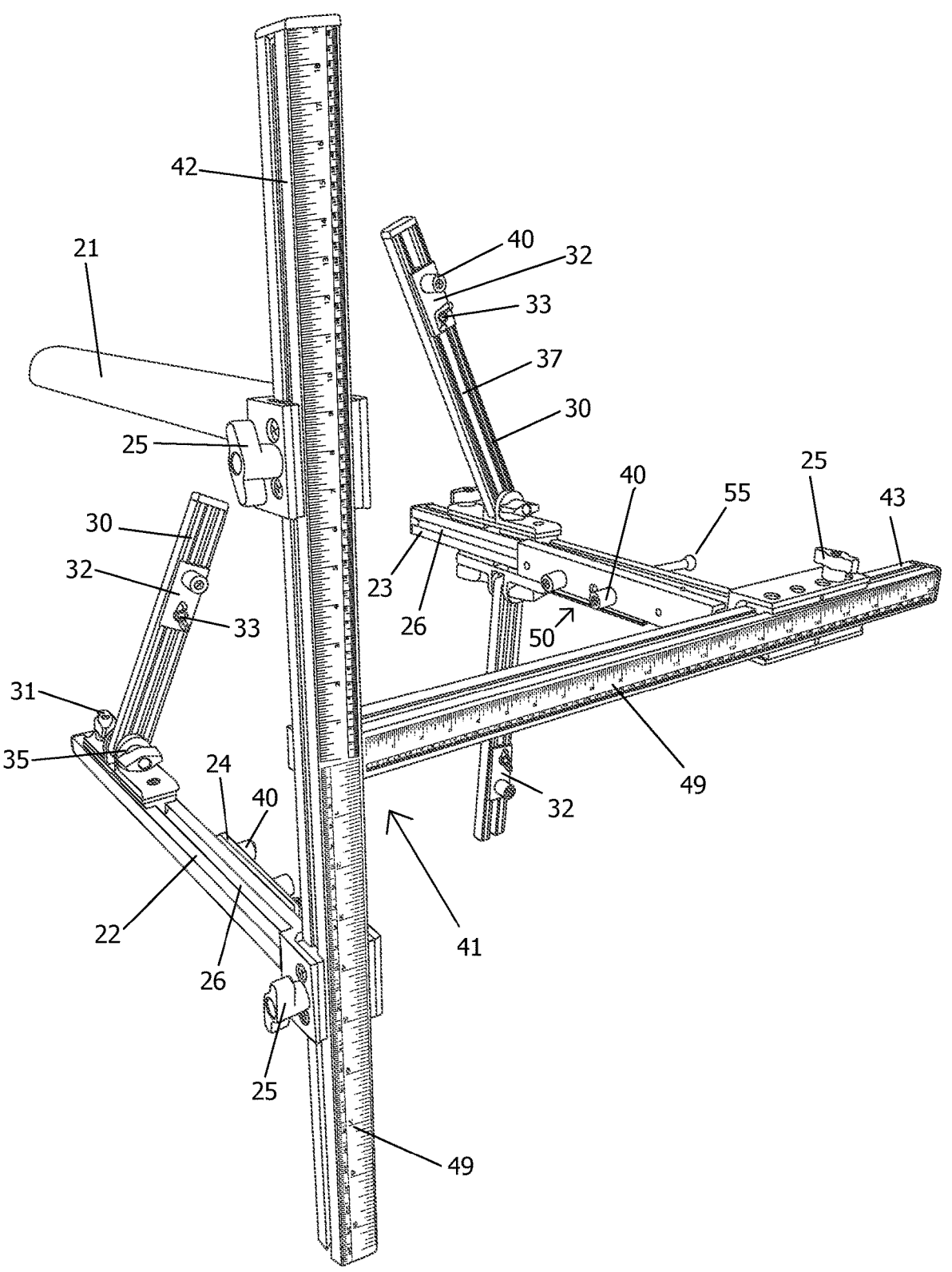
FIG. 1 is a left rear perspective view of an embodiment of an orthopedic device without contact panels pictured.
Figure 2:
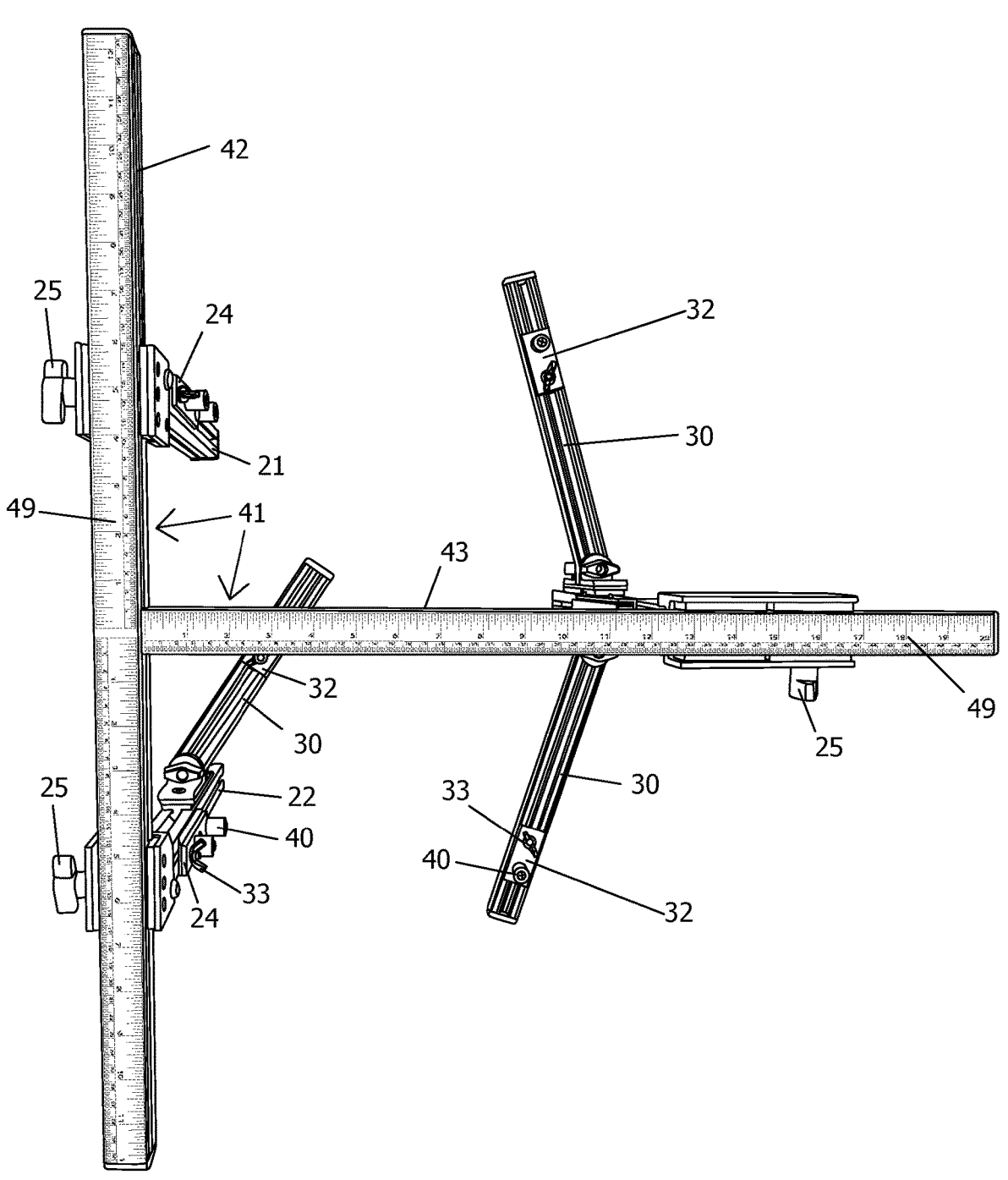
FIG. 2 is a rear view of the orthopedic device of FIG. 1.
Figure 3:
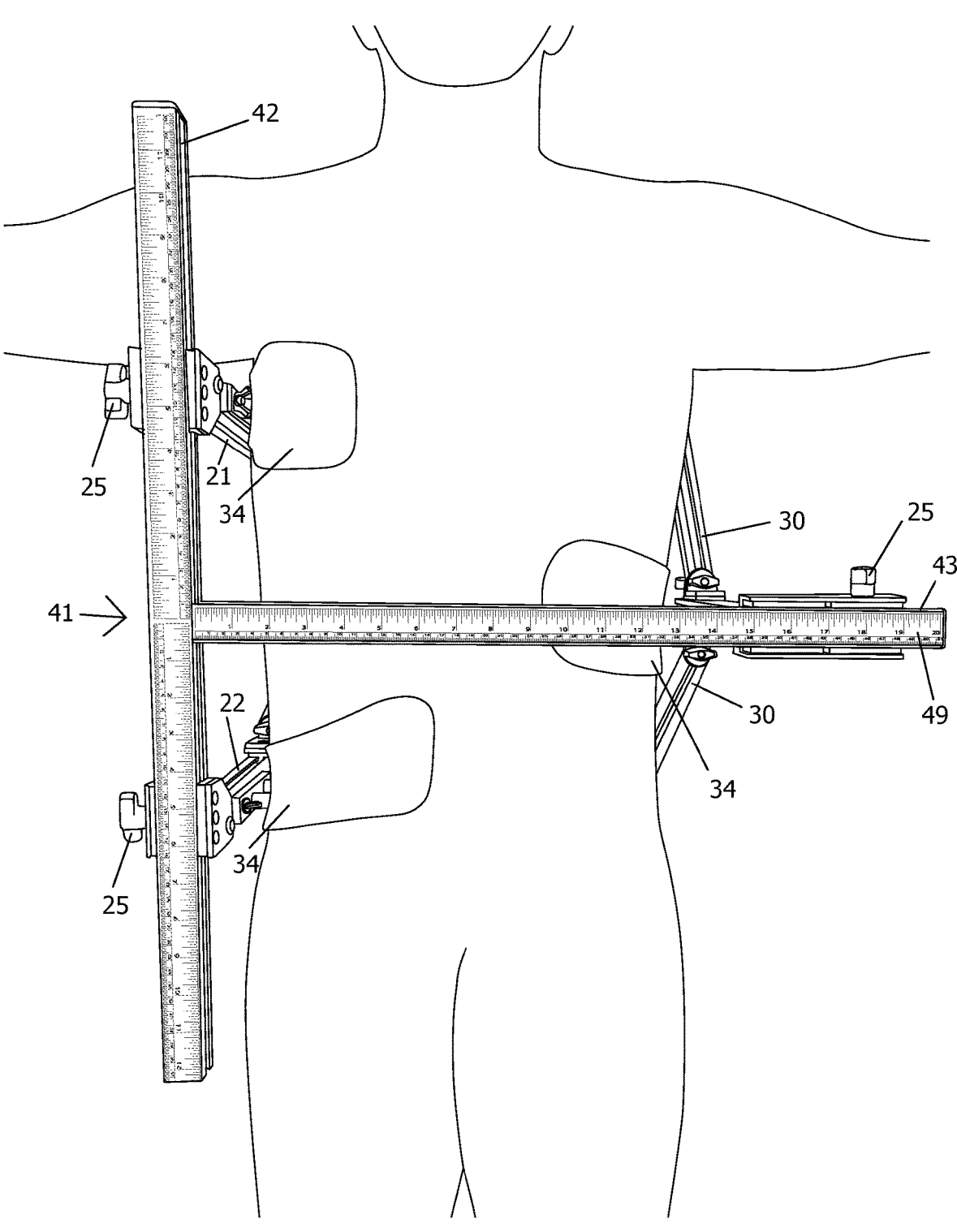
FIG. 3 is a rear view of an embodiment of an orthopedic device positioned on a user with the device oriented and configured for alignment of a scoliosis curve with a right thoracic apex or a double scoliosis curve with a right thoracic apex and a left lumbar apex.
Figure 4:
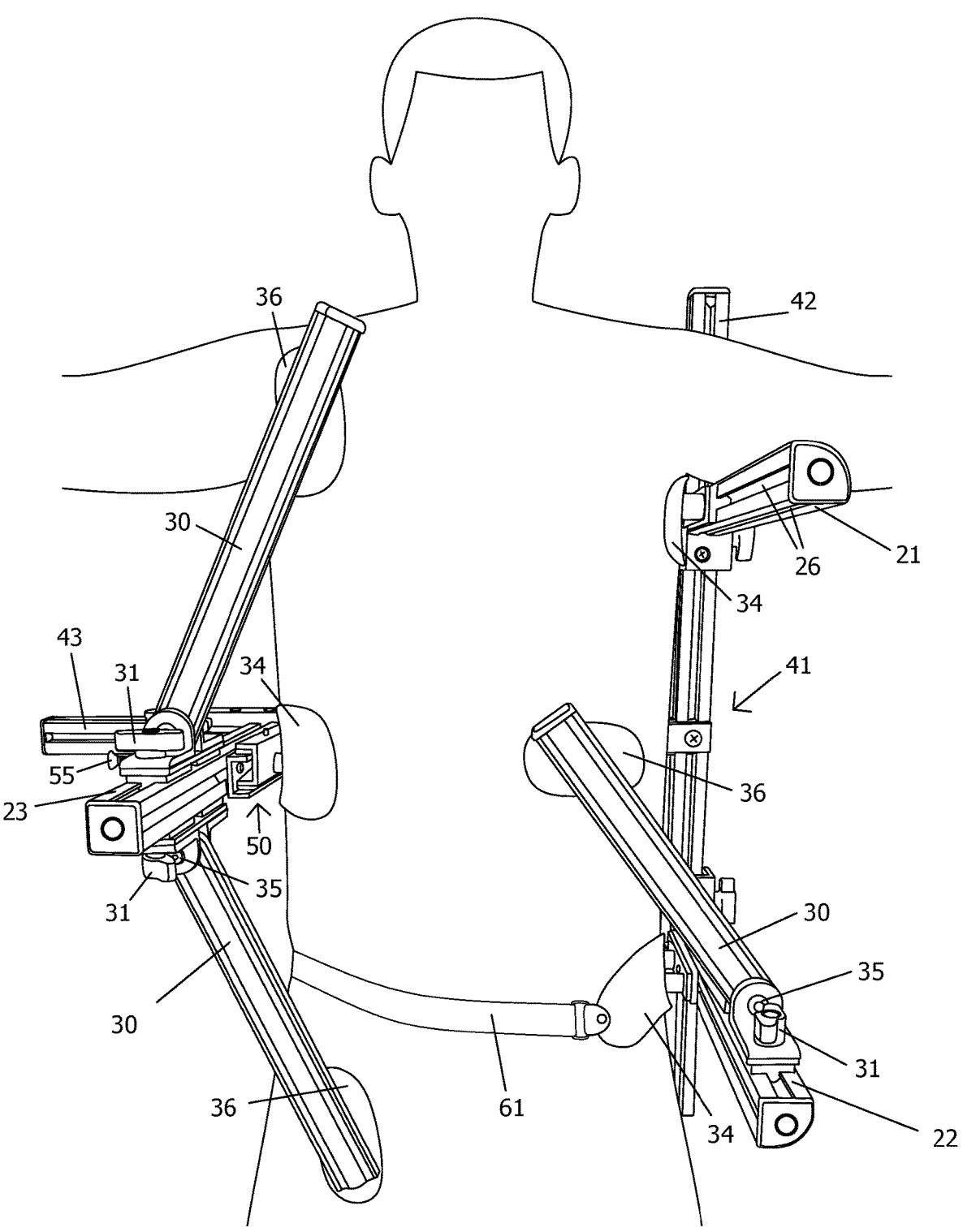
FIG. 4 is a front view of the orthopedic device of FIG. 3 with three adjustable arms and six contact panels in view.
Figure 5:
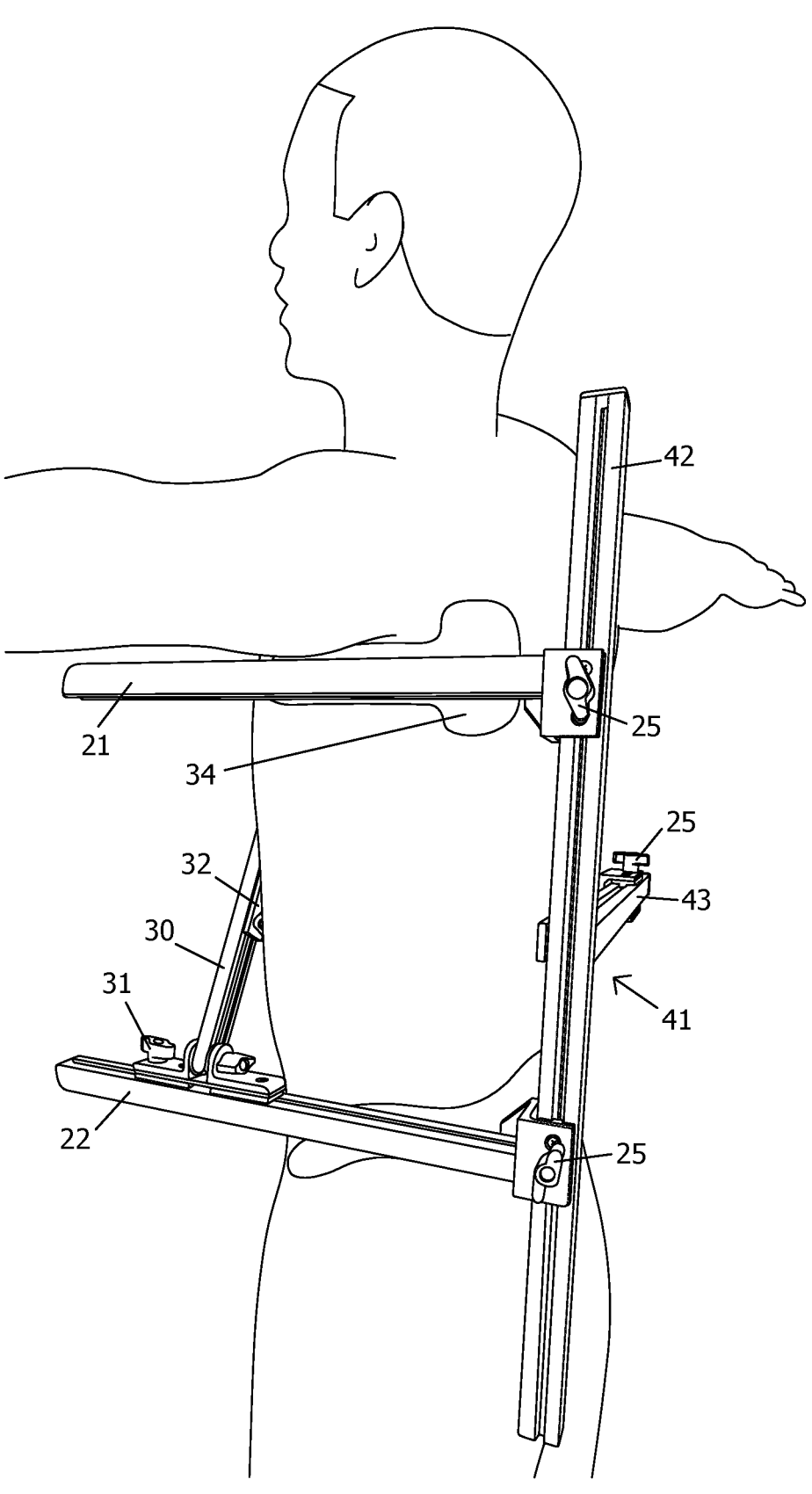
FIG. 5 is a left perspective view of the orthopedic device of FIG. 3.
Figure 6:
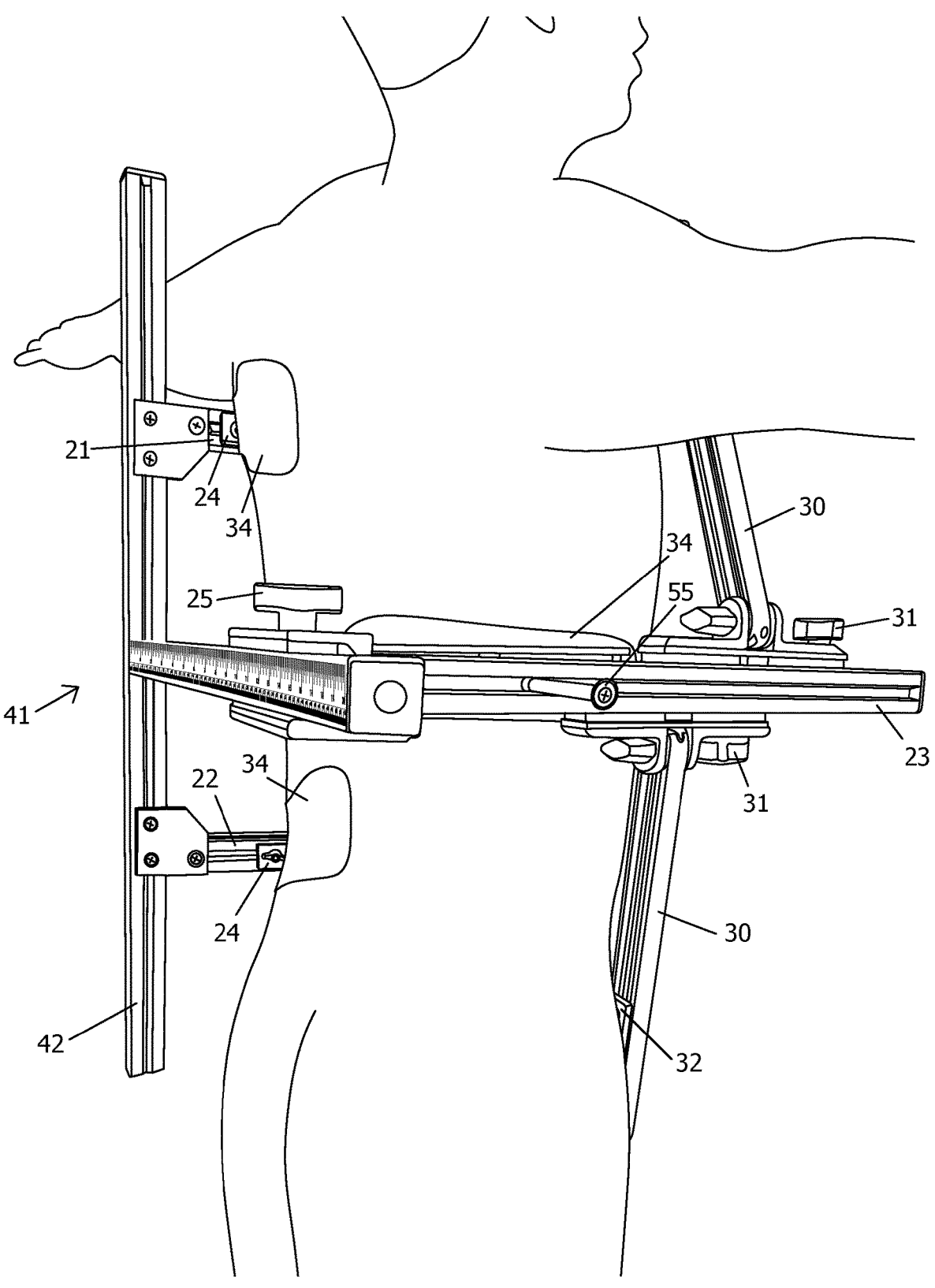
FIG. 6 is a right perspective view of the orthopedic device of FIG. 3.
Figure 7:
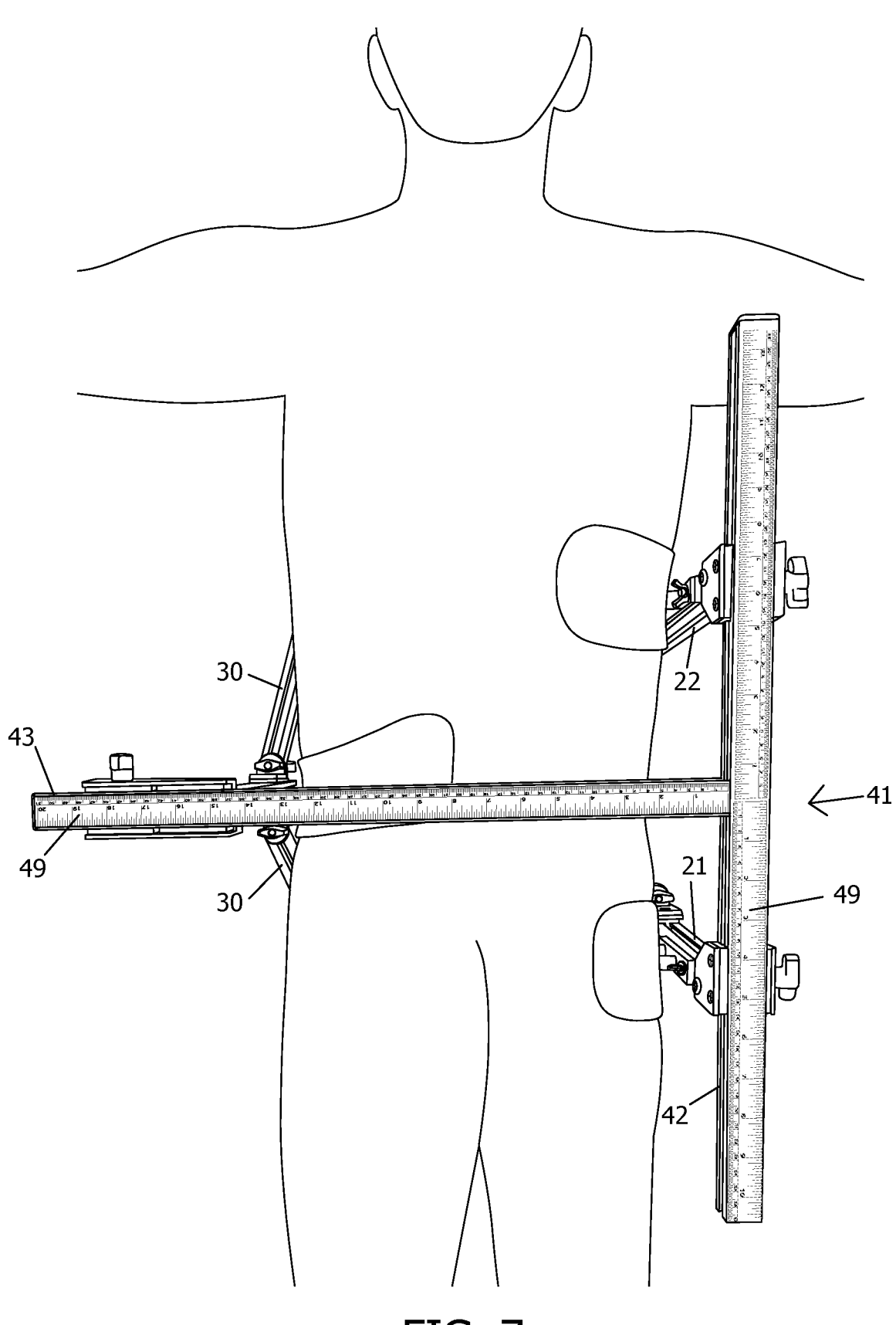
FIG. 7 is a rear perspective view of the orthopedic device of FIG. 3 positioned on a user with the orthopedic device oriented and configured for alignment of a scoliosis curve with a left lumbar apex. Contact panels are applied to the right thoracic region, the right pelvic area, and the left lumbar region.
Figure 8:
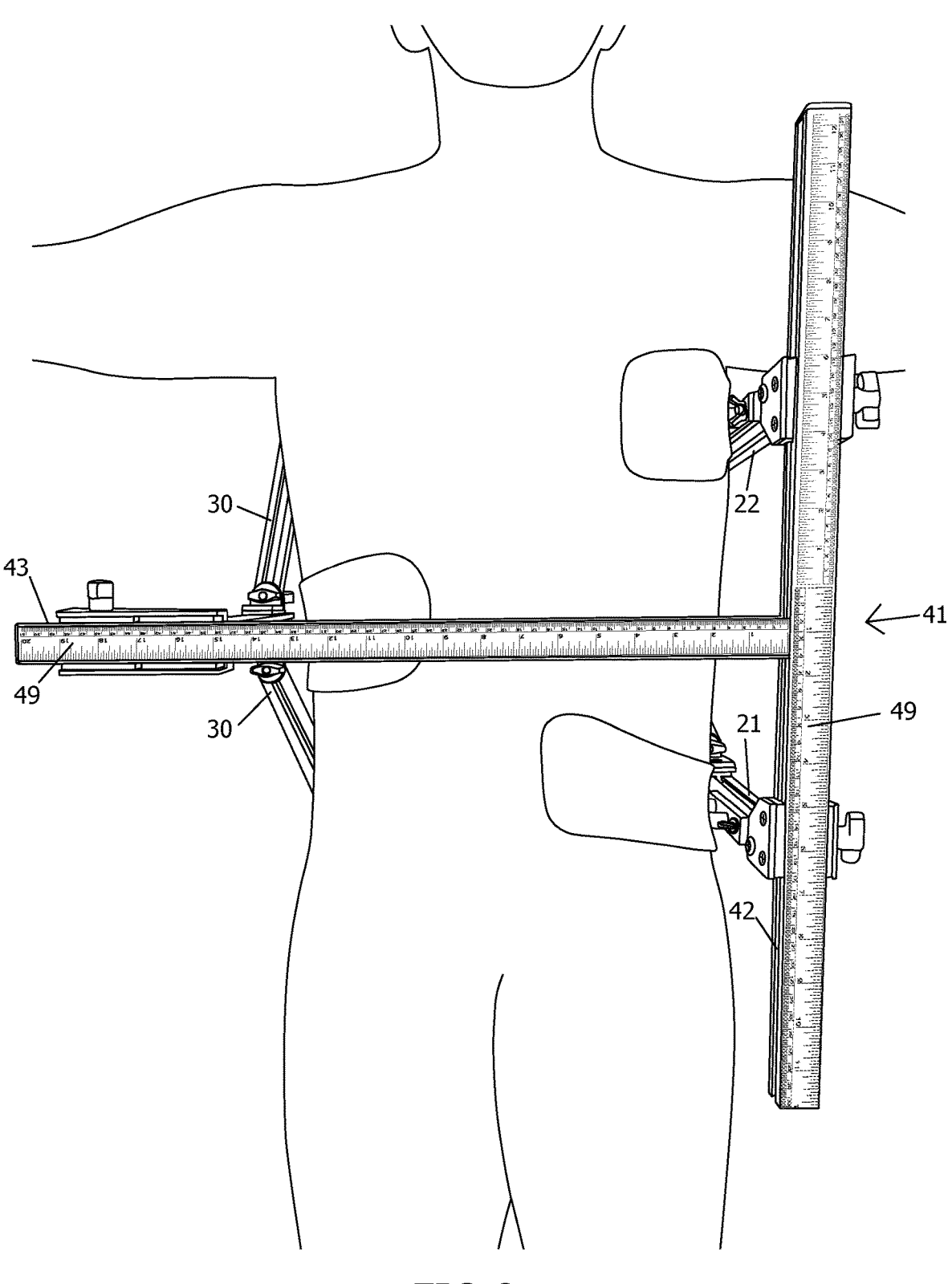
FIG. 8 is a rear perspective view of the orthopedic device of FIG. 3 positioned on a user with the orthopedic device oriented and configured for alignment of a scoliosis curve with a left thoracic apex, or a double scoliosis curve with a left thoracic apex and a right lumbar apex. A contact panel is applied to each of the following regions: the right axillary region, the right lumbar area, and the left thoracic region.
Figure 9:
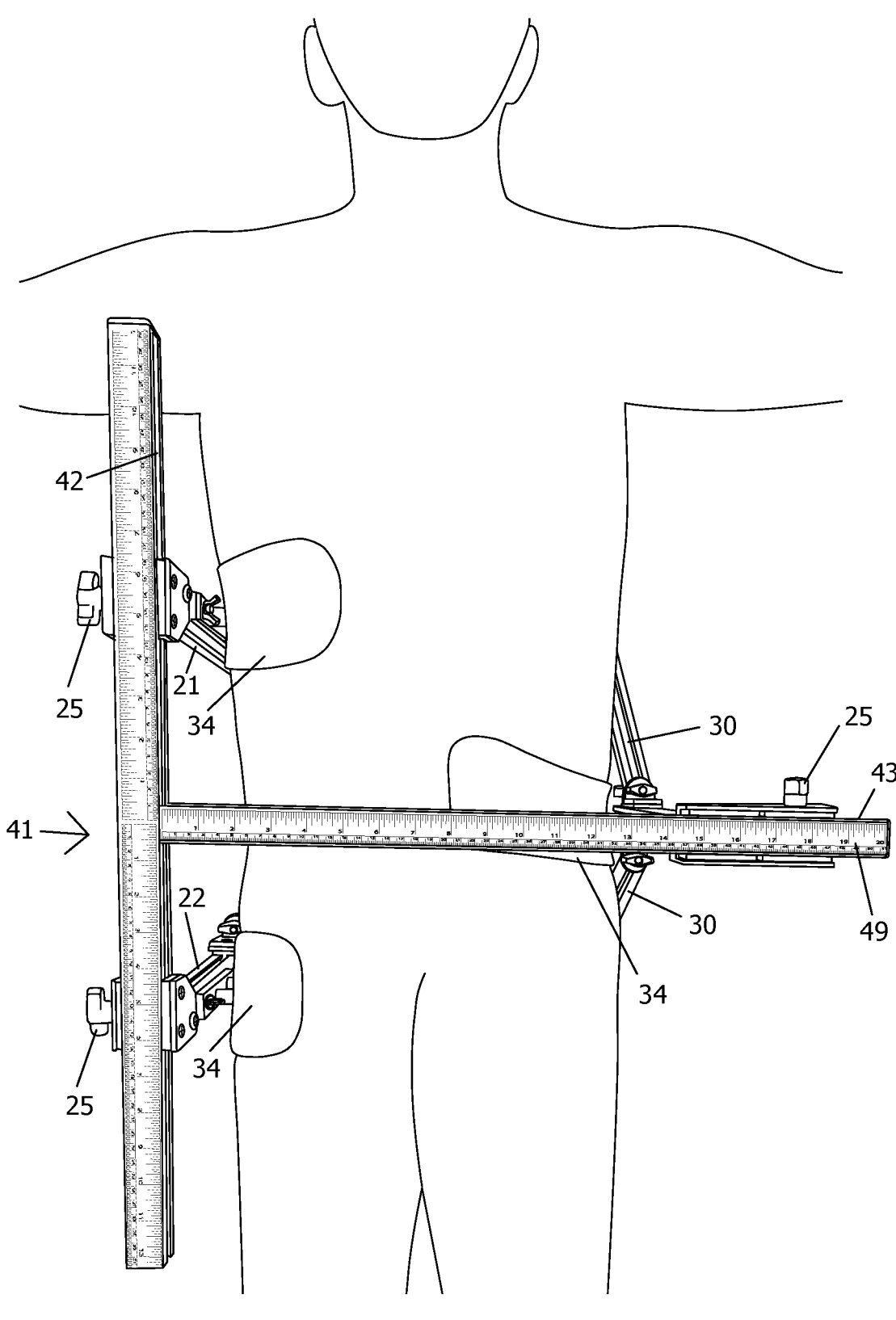
FIG. 9 is a rear perspective view of the orthopedic device of FIG. 3 positioned on a user with the orthopedic device oriented and configured for alignment of a scoliosis curve with a right lumbar apex. A contact panel is applied to each of the following regions: the left thoracic region, the left pelvic region, and the right lumbar region.
Figure 10:
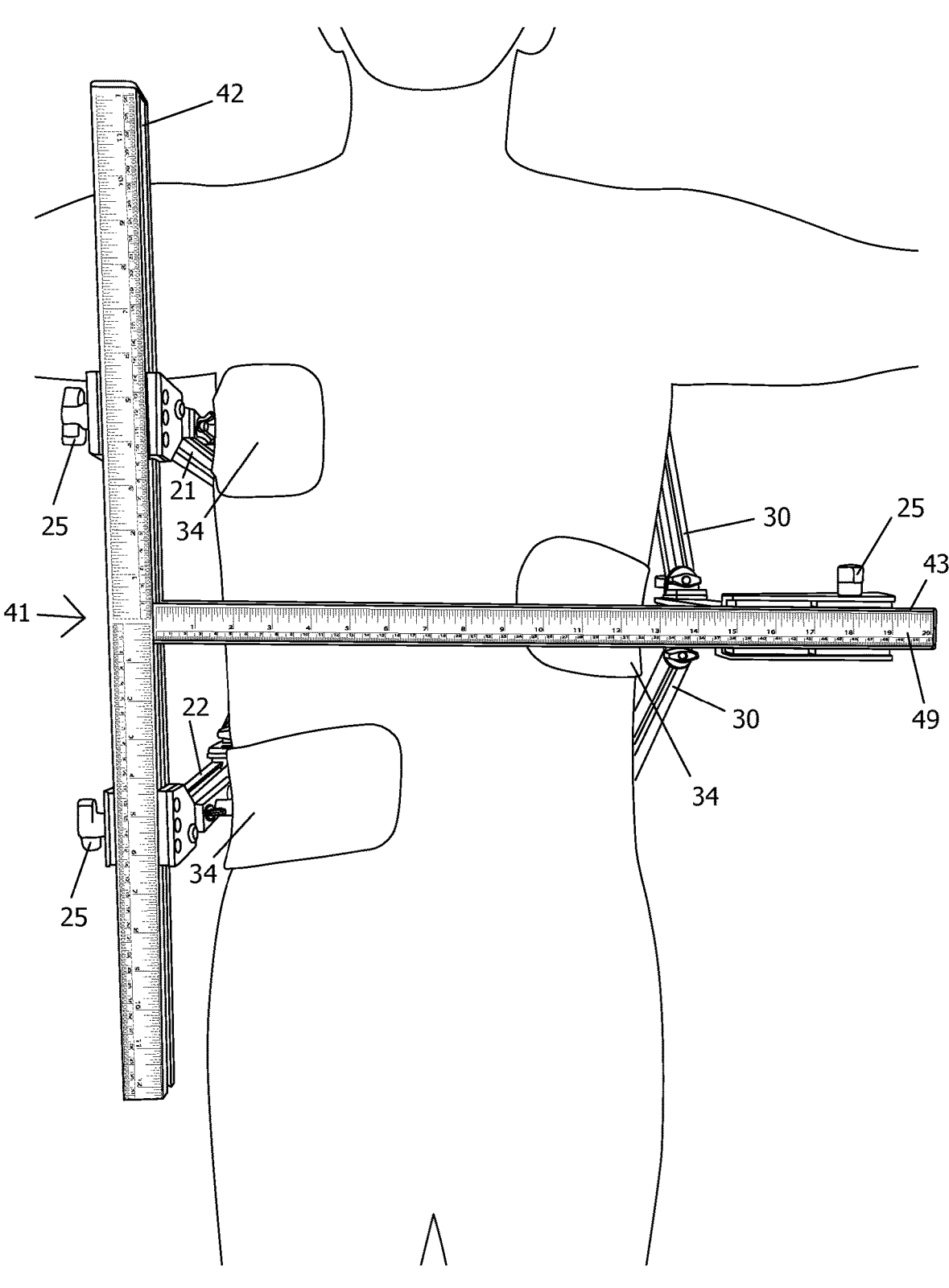
FIG. 10 is a rear perspective view of the orthopedic device of FIG. 3 positioned on a user with the orthopedic device oriented and configured for alignment of a scoliosis curve with a right thoracic apex and a Left thoracolumbar apex. A contact panel is applied to each of the following regions: the left axillary region, the left thoracolumbar region, and the right thoracic region.

The device according to the present disclosure provides an apparatus with which to measure, position, align, realign, approximate, assess, hold, suspend, compress, extend, cue, inhibit, and/or facilitate a patient for the purpose of assessing or treating a musculoskeletal condition in a manner that is effective, quantitative, and/or reproducible relative to traditional methods.

Overview

Some embodiments of the current invention are discussed in detail below. In describing embodiments, specific terminology is employed for the sake of clarity; however, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

A better understanding of different embodiments of the invention may be had from the following description read with the accompanying drawings in which like reference characters refer to like elements.

For further ease of understanding the embodiments of an orthopedic device and variants as disclosed, a description of a few terms is necessary. As used, the term "posterior" has its ordinary meaning and refers to a location behind or to the rear of another location. The term "anterior" has its ordinary meaning and refers to a location ahead of or to the front of another location. The term "superior" has its ordinary meaning and refers to a location above or over top of another location. The term "inferior" has its ordinary meaning and refers to a location below or under another location. The term "Right" and "Left" have their meaning relative to the orthopedic device user's anatomical right and left. The anatomical terms described herein are not intended to detract from the normal understanding of such terms as readily understood by one of ordinary skill in the art of orthopedics.

The term "semi-rigid" may be used to connote properties that provide stiffness, support and are free-standing; however components that possess such properties may have some degree of flexibility and resiliency.

The embodiments of the disclosure are adapted for a human body, and may be dimensioned to accommodate different body types, shapes, proportions and sizes of humans as well as for animal species other than homosapian. For explanatory purposes, the orthopedic device embodiments described are referred to as corresponding to different sections and features of a human body and are denoted by general anatomical terms for the human body.

Various Embodiments of the Orthopedic Device

In an embodiment shown in FIGS. 3-10, an orthopedic device is provided for, among other functions, measuring and positioning the alignment of a deformed human spine in frontal, sagittal and/or transverse planes toward that of a structurally and physiologically normal spine.

A frame assembly 41 comprises at least two frame members. In the embodiment of FIGS. 3-10 the frame assembly 41 comprises a perpendicular frame member 43 having a first end and a second end and a parallel frame member 42 having a first end, and a second end, wherein the perpendicular frame member 43 is rigidly coupled by its first end to the parallel frame member 42. The perpendicular frame member 43 is oriented perpendicular to the parallel frame member 42.

The device according to the present disclosure comprises at least three primary extensions each having a mount end and a free end. In the embodiment of FIGS. 3-10, a first primary extension 21 having a mount end and a free end is slidably coupled by its mount end to the parallel frame member 42 between the first end of the parallel frame member 42 and the location on the parallel frame member 42 at which the perpendicular frame member 43 is coupled. A second primary extension 22 having a mount end and a free end is slidably coupled by its mount end to the parallel frame member 42 between the second end of the parallel frame member 42 and the location on the parallel frame member 42 at which the perpendicular frame member 43 is coupled. A third primary extension 23 having a mount end and a free end is slidably coupled by its mount end to the perpendicular frame member 43.

According to the present disclosure, each of the at least three primary extensions comprise at least one slot 26, the slots 26 running parallel to the long axis of the respective primary extension. In the embodiment of FIGS. 3-10, each of the first and second primary extensions 21,22 define two slotted surfaces, the slots 26 running parallel to the long axis of the respective primary extension. The third primary extension 23 defines four slotted surfaces, the slots 26 running parallel to the long axis of the third primary extension 23.

In the embodiment of FIGS. 3-10, each of the first, second, and third primary extensions 21, 22, 23, are oriented substantially perpendicular to both the parallel frame member 42, and the perpendicular frame member 43 and remain in the perpendicular orientation thereof regardless of their coordinates relative to the respective frame members to which they are slidably coupled. Additionally, each of the first, second, and third primary extensions 21,22,23 remain substantially parallel to one another regardless of their relative coordinates along the axis of the respective frame members to which they are slidably coupled. Each of the first, second, and third primary extensions 21,22,23 are configured to lock in a selected position along the length of the slot of the respective frame members to which they are slidably coupled via thumb screws 25.

The device according to the present disclosure comprises at least one sliding fixture 24 having a first end and a second end, and having a projection side 27 and a panel side 28. The projection side 27 of the sliding fixture 24 is configured to slideably mount to and selectively lock in-place on the at least one slot 26 defined by any one of the at least three primary extensions 21, 22, 23. The device according to the present disclosure further comprises at least one contact panel 34, configured with a contour to accommodate the surface anatomy of the region to which the contact panel 34 is applied. The at least one contact panel 34 is configured to mount on the at least one sliding fixture 24.

In the embodiment of FIGS. 3-10 one sliding fixture 24 is disposed on one slot 26 defined by each of the first and the second primary extensions 21,22. The position of each sliding fixture 24 is adjustable along the length of the slots 26 of the first and second primary extensions 21,22 running parallel to the long axis of its respective primary extension. Additionally, each sliding fixture 24 is configured to selectively lock in an unlimited number of positions along the length of the slots 26 of the first and the second primary extensions 21,22. A thumb screw 33 placed through a hole defined by the sliding fixture toward the second end of the sliding fixture is configured to selectively lock the position of the sliding fixture 24.

In the embodiment of FIGS. 3-10 contact panels 34 are configured to fasten to the sliding fixtures 24. The contact panels 34 comprise semi-rigid to rigid panels contoured to accommodate the shape of the region of the user's body to which they are intended to contact, such that forces are distributed across the contact panel 34. In the embodiment of FIGS. 3-10, spacers 40 are positioned between the contact panels 34 and the sliding fixtures 24. While the embodiment of FIGS. 3-10 depicts spacers 40 being positioned between the contact panels 34 and sliding fixtures 24, other means for fastening the contact panels 34 to the sliding fixtures 24 may be employed.

In the embodiment of FIGS. 3-10, a parallel extender assembly 50 is adjustably mounted to the third primary extension 23. In the embodiment of FIGS. 3-10, the parallel extender assembly 50 comprises a stationary plate 51, the stationary plate being adjustably mounted to the third primary extension 23, four struts 53, each strut having a first end and a second end, a moving plate 52, an adjustment shaft 55 having a first end and second end, and an adjustment shaft engager 54 having a cylindrical body and a threaded hole through the body thereof. The stationary plate 51, is pivotally attached to four struts 53 by the first end of the struts 53. Each strut 53 rotates about one axis relative to the stationary plate 51, the axis of rotation of each strut 53 being substantially parallel to the axis of rotation of the other three struts 53.

The moving plate 52 is coupled to the second end of the four struts 53, each strut 53 rotating about one axis relative to the moving plate 51. The axis of rotation of each strut 53 relative to the moving plate is substantially parallel to the axis of rotation of each strut 53 relative to the stationary plate 51.

In the embodiment of FIGS. 3-10, the form of the adjustment shaft engager 54 is consistent with that of a dowel nut. The adjustment shaft engager 54 is rotatably fit into a hole defined by the third primary extension 23, the third primary extension 23 defining a slot, the slot being oriented to allow movement of the adjustment shaft 55 through the threaded hole of the adjustment shaft engager 54.

In the embodiment of FIGS. 3-10, rotation of the adjustment shaft 55 about the long axis of the adjustment shaft, adjusts the length of the adjustment shaft between the adjustment shaft engager 54 and the moving plate 52. The second end of the adjustment shaft 55 is substantially rounded, and interfaces with the moving plate 52 via an indentation in the moving plate 52 that matches the second end of the adjustment shaft 55. The adjustment shaft 55 is able to rotate about the long axis thereof 55, and rotate about the axis of the cylindrical body of the adjustment shaft engager 54 while the second end of the adjustment shaft 55 remains in the indentation of the moving plate 52.

While this embodiment depicts the parallel extender assembly 50 as using four pivoting struts 53, a parallel extender assembly 50 may employ any number of struts 53.

The embodiment of FIGS. 3-10 depicts the adjustment shaft as a threaded machine screw; however, an adjustment shaft may employ an alternate form with or without threads.

The embodiment of FIGS. 3-10 depicts the adjustment shaft engager as a dowel nut; however an adjustment shaft engager may employ an alternate form, with or without threads, for controlling the position of the adjustment shaft relative to the component to which the adjustment shaft engager is coupled.

In the embodiment of FIGS. 3-10, the contact panel 34 is mounted to the moving plate 52 with spacers 40 positioned between the contact panel 34 and the moving plate 52. While the embodiment of FIGS. 3-10 depicts spacers 40 being positioned between the contact panel 34 and the moving plate 52, other means for fastening the contact panel 34 to the moving plate 52 may be employed. Additional dowel nut holes may be placed along the length of the primary extension to which the parallel extender assembly 50 is coupled in order to adjust the position of the parallel extender assembly 50 on the primary extension to which it is coupled.

In the embodiment of FIGS. 3-10 the parallel extender assembly 50 is configured to adjust the position of the contact panel 34 mounted on the moving plate 52 along an arced path relative to the third primary extension 23 and the frame assembly 41. The radius of the arced path is defined by the length of the struts 54. In the embodiment of FIGS. 3-10, the position of the moving plate 52 relative to the stationary plate 51 is adjustable in an infinite number of increments by the adjustment shaft 55.

Figure 11:
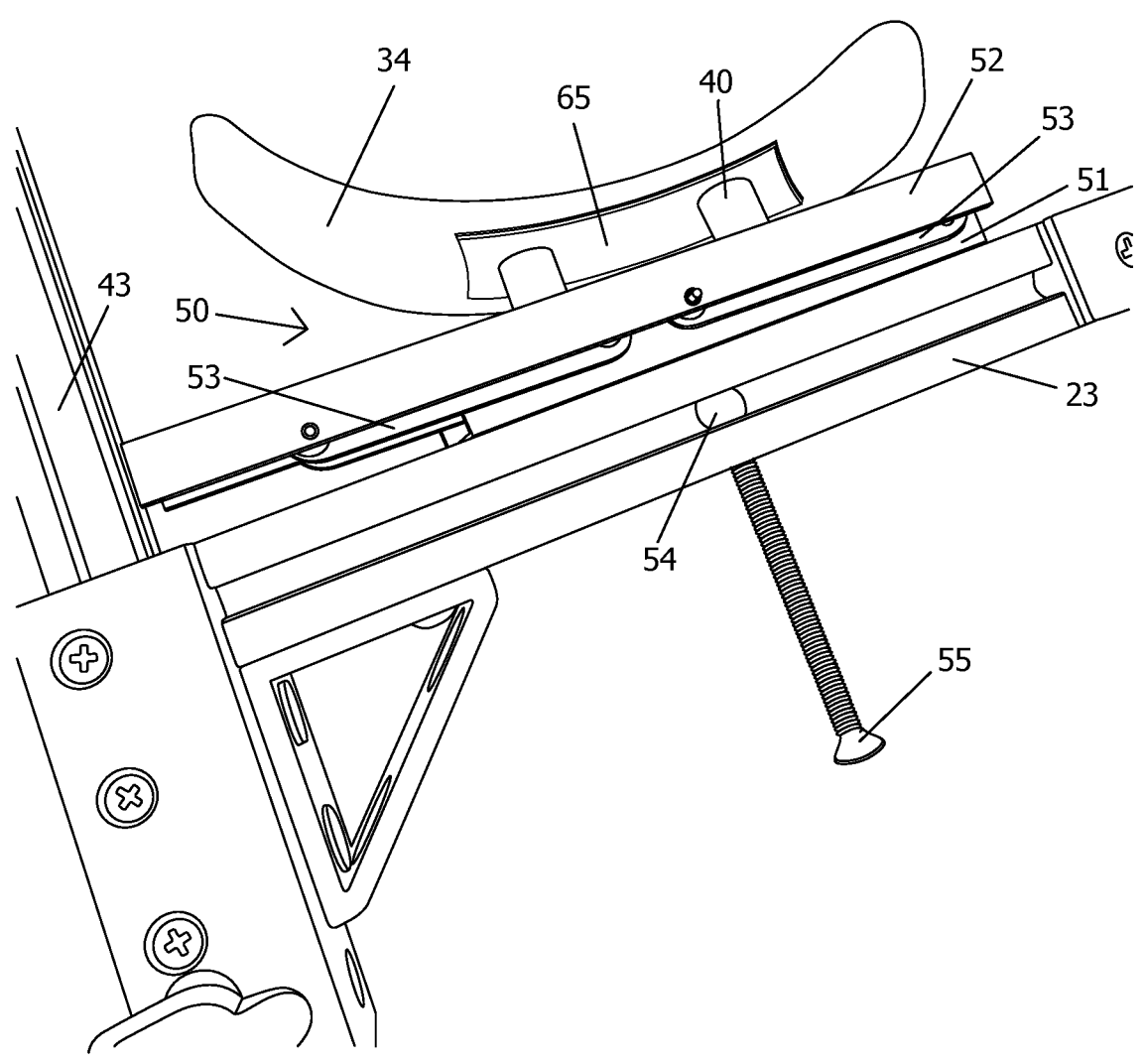
FIG. 11 is a top perspective view of a parallel extender assembly with a force plate between the contact panel and the contact panel spacers, with the assembly in a retracted position.
Figure 12:
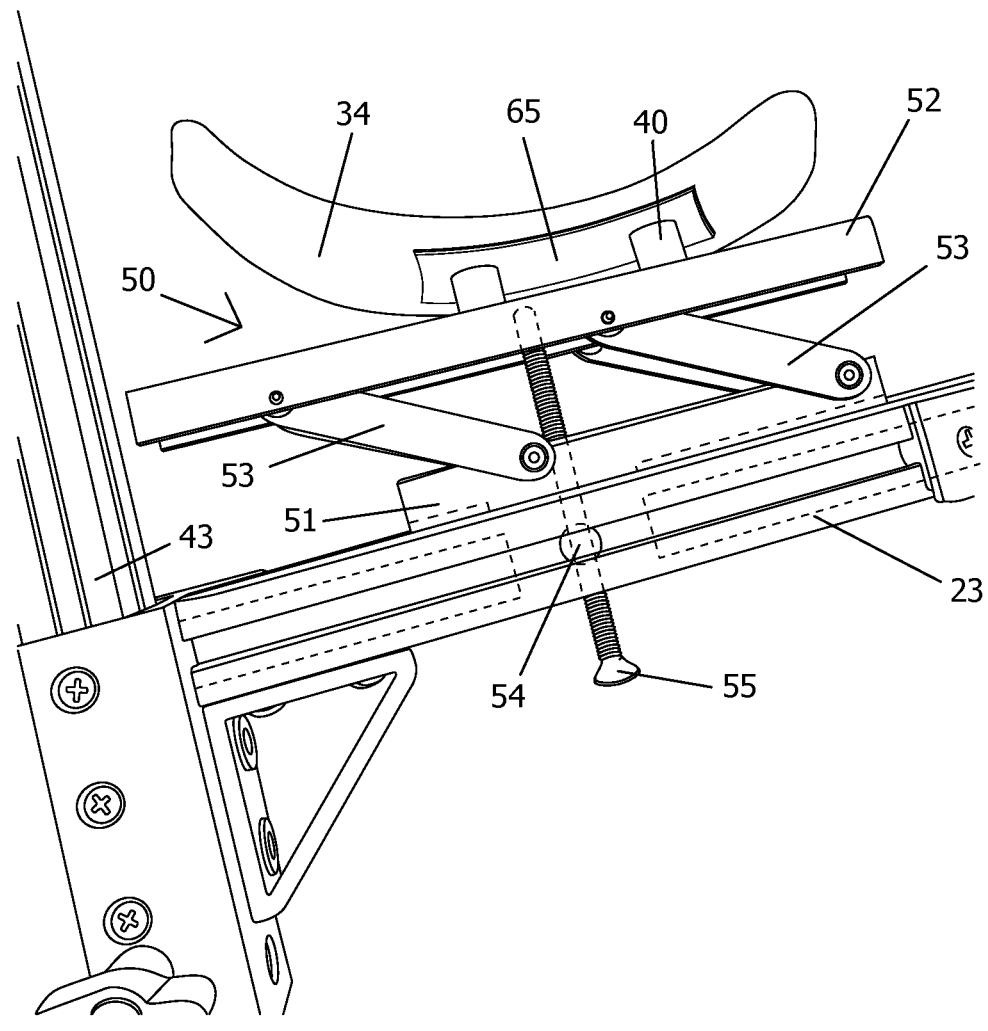
FIG. 12 is a top perspective view of the parallel extender assembly of FIG. 11 in an extended position.

FIG. 11 depicts a force plate 65 of the embodiment of FIGS. 3-10 mounted between the moving plate 52 and the contact panel 34.

In the embodiment of FIG. 3-10, three adjustable arms 30 are configured to slidably mount to combinations of the first, second, and third primary extensions 21, 22, 23 via slots 26 defined by the primary extensions thereof. Each of the three adjustable arms 30 has a mount end and a free end, the mount end thereof being slidably mounted to one of the three primary extensions 21, 22, 23. In the embodiment of FIGS. 3-10, one of the three adjustable arms 30 is slidably mounted to the second primary extension 22 and two of the three adjustable arms 30 are slidably mounted to the third primary extension 23. While the embodiment of FIGS. 3-10 depicts the aforementioned combination of adjustable arms 30, the embodiment thereof is configured for between zero and six adjustable arms 30 to slidably mount to any combination of the first primary extension 21, second primary extension 22, and third primary extension 23.

In the embodiment of FIGS. 3-10, each adjustable arm 30 is configured to allow a linear adjustment of its position along the slot 26 of the primary extension to which it is coupled. The position of each adjustable arm 30 along the defined slots 26 are lockable via thumb screws 31. Each adjustable arm 30 defines a pivoting joint 35 around which the angle of the free end of the adjustable arm is adjustable relative to the mount end of the adjustable arm 30. The axis of rotation of the pivoting joint 35 of the adjustable arm 30 is parallel to the long axis of the primary extension 21, 22, 23 to which the adjustable arm 30 is slidably mounted. Each adjustable arm's pivoting joint 35 is selectively lockable via a locking screw.

In the embodiment of FIGS. 3-10, the surface of each adjustable arm 30 facing the mount end of the primary extension to which the adjustable arm 30 is slidably mounted defines a slot 37 oriented parallel to the long axis of the adjustable arm 30. A sliding fixture 32 is slidably mounted to the adjustable arm 30 via the slot 37 thereof. Contact panels 36 are mounted to the sliding fixtures 32. The position of the sliding fixtures 32 are selectively lockable along the slot to which the sliding fixture 32 mounts via a thumb screw 33.

A linear scale 49 may be placed or engraved on at least one surface of the parallel and/or perpendicular frame member(s) 42,43, and may also be placed or engraved on at least one surface of the primary extensions 21,22,23. In the embodiment of FIGS. 3-10 a linear scale 49 is placed or engraved on the posterior surface of the parallel and perpendicular frame members 42,43.

The linear scale 49 placed or engraved on the frame assembly is configured for measuring the distances between contact panels 34. In other embodiments, linear scales placed or engraved on the surface of primary extensions configured for measuring the distance between contact panels 34, 36 may be employed.

The device according to the embodiment of FIGS. 3-10 may be completely supported by the user while the device is in use made possible by the friction of the contact panels 34,36 applying compressive force on the external surface of the user's body. The device according to the embodiment of FIGS. 3-10 may also be supported through a combination of the aforementioned friction and a supplemental waist strap 61 fastened to the contact panel 34 positioned closest to the user's waist to augment the support provided by the friction of the contact panels 34,36 on the user's body. The device according to the embodiment of FIGS. 3-10 may also be partially supported by cord(s) fastened to hardware on the surface of one or more of the frame members 42,43 or one or more of the primary extensions 21,22,23. The elastic cord is positioned to evenly support only the weight of the device without creating any additional force vectors that would influence the position of the user.

The device according to the embodiment of FIGS. 3-10 may be configured to use with the frame assembly 41 on a horizontal surface with the primary extensions 21, 22, 23 in a vertical position. Spacers may be attached to the side of the frame assembly 41 that would otherwise touch the horizontal surface to space the frame assembly 41 away from the horizontal surface thereby increasing the ease with which the primary extensions 21, 22, 23 may be adjusted on the frame assembly.

Operation of the Embodiment of FIGS. 3-10

The embodiment of FIGS. 3-10 is configured to move the users torso into a position in which the user's scoliotic spine is closer to that of a physiologically normal spine via the change in position of the contact panels 34,36, and the effect thereof on the user's body position.

The first step in operating the embodiment of FIGS. 3-10 is to determine how the device will be oriented and where the primary extensions 21,22,23 will be positioned relative to the user's body for application in later steps after the appropriate contact panels 34 have been mounted.

The device will be oriented such that the frame assembly 41 is positioned posterior to the user's torso, with the primary extensions 21,22,23 positioned lateral to the user's torso with the first and second primary extension 21,22 on the side of user's torso opposite that of the scoliosis curve apex targeted for treatment, and the third primary extension 23 on the same lateral side of the user's torso as the scoliosis curve apex that is targeted for treatment. The second ends of the first, second and third primary extensions 21,22,23 will project posteriorly of the user's torso, and the first ends of the primary extensions 21,22,23 thereof will project anterior of the user's torso.

The relative height at which each primary extension 21,22,23 should be positioned to interface with the user's body via contact panels 34 must be determined and will vary depending on the characteristics and location of the scoliosis curve and the scoliosis curve's apex.

If the targeted scoliosis curve's apex is to the user's anatomical right, the height at which the first primary extension 21 and second primary extension 22 should be positioned at the left lateral midline of the user's torso is at the height corresponding to the vertebrae considered to be the top of the scoliosis curve and the bottom of the scoliosis curve respectively. The height at which the third primary extension 23 should be positioned at the right lateral midline of the user's torso is at the height corresponding to the apical vertebrae.

If the apex of the scoliosis curve targeted for treatment is to the patient's left, then the position of the frame assembly 41 should be altered from the aforementioned description by 180 degrees in the frontal plane such that the first and second primary extension 21,22 are positioned on the right lateral midline of the user's torso. Additionally, the relative positions of the first primary extension 21 and the second primary extension 22 reverse compared to the aforementioned description—the first and second primary extensions 21,22 are positioned at the height of the bottom and top vertebrae of the scoliosis curve respectively.

If compensatory scoliosis curve(s) exist at the top and/or the bottom of the scoliosis curve targeted for treatment (with an apex to the side of the user's torso opposite that of the scoliosis curve targeted for treatment), then the primary extensions 21,22 that correspond to the top and bottom of the scoliosis curve targeted for treatment should be positioned at the lateral midline of the user's torso at the height corresponding to the vertebrae considered the apex of the compensatory scoliosis curve.

After the orientation of the frame assembly 41, and position of the primary extensions 21,22,23 have been determined, a contact panel 34 is fastened to each of the first and second primary extensions 21,22 via a sliding fixture 24, and a contact panel 34 is fastened to the third primary extension 23 via the parallel extender assembly 50. Each contact panel 34 is contoured and shaped to accommodate the user's body in the intended location corresponding to the predetermined height of the respective primary extension 21,22,23.

After contact panels 34 have been fastened to the sliding fixtures 24 and the parallel extender assembly 50, the frame assembly 41 is positioned posterior to the user as heretofore described, and the primary extensions 21,22,23 are adjusted to the predetermined heights relative to the users body as heretofore indicated in the following manner: The contact panel 34 of the third primary extension 23 is placed on the lateral and posterolateral region of the user's torso that corresponds to the height of the apical vertebrae of the scoliosis curve targeted for treatment. With the device stabilized to maintain the contact panel 34 of the third primary extension 23 in position thereof, the relative height of the first and second primary extensions 21,22 are then adjusted on the parallel frame member 42 to the move the first and second primary extensions 21,22 and their corresponding contact panels 34 to the predetermined height, heretofore described, on the users body.

Next, the third primary extension 23 is adjusted medially on the perpendicular frame member 43 so that the corre-sponding contact panel 34 contacts and applies positive force at the intended location on the user's torso at the height corresponding to the apex of the scoliosis curve. The position of the third primary extension 23 on the perpendicular frame member 43 is then locked via thumb screw 25.

In the embodiment of FIGS. 3-10, the next step is to move the adjustable arms 30 into a position that places the contact panels 36 in the desired location on the user's body to reduce the user's skeletal asymmetries that have resulted from vertebral rotation. The placement of the contact panels 36 thereof also stabilizes the rotational orientation of the user's body during the final adjustment of the contact panel 34 of the third primary extension 23 described hereafter. The exact placement of the adjustable arms 30 and contact panels 36 will vary on a case by case basis depending on the clinical presentation of the user and the areas where asymmetries resulting from vertebral rotation are most apparent and clinically relevant. Locations in which the contact panels 36 may be commonly placed in treatment of a right thoracic scoliosis curve, for example, are the anterior portion of the left 7th & 8th rib and costal arch, the anterior aspect of the right shoulder at coracoid process and pectoralis minor tendon, and the anterior aspect of the left and/or right side of the pelvis between the anterior superior iliac spine and the pubis.

The contact panels 36 are positioned by, first, rotating the adjustable arm 30 so that the adjustable arm 30 is directly anterior to the desired asymmetric location on the user's body; second, adjusting the contact panel 36 along the adjustable arm's slot 37 so that the contact panel 36 is directly anterior to the desired location on the user's body with the asymmetry; third, with the adjustable arm thumb screw 31 unlocked, moving the adjustable arm 30 linearly in an anterior to posterior direction until the contact panel 36 has moved the prominent aspect of the user's body into a position of acceptable symmetry by derotating that segment of the user's torso. Once the user is in the desired position, the adjustable arm thumb screw 31 is locked.

The final adjustment of the device, according to the embodiment of FIGS. 3-10, is moving the contact panel 34 of the third primary extension 23 anteromedially via the parallel extender assembly 50 by tightening the adjustment shaft 55 until one of the following occurs: the discomfort tolerance of the user has been reached, or it has been determined that the user's spine has reached optimal alignment.

The device according to the embodiment of FIG. 3-10 can be used for various purposes. Goals that can be achieved through application of the device according to the embodiment of FIG. 3-10 include but are not limited to: a digital optical 3D scan can be performed of the user with the device applied in order to fabricate an orthopedic brace for treatment of the spinal deformity; a radiograph of the user's spine can be conducted with the device applied to determine if the patient's spine possesses sufficient flexibility for an orthopedic brace to effectively align the user's spine; a plaster cast may be applied prior to application of the device and the device and cast removed once the plaster begins to harden to use the plaster cast in fabrication of an orthopedic brace for treatment of the spinal deformity; a plaster cast may be applied prior to application of the device for the purposes of serial plaster casting treatment and the device removed once the plaster has hardened; the device according to FIGS. 3-10 may be directly used to brace a user in treatment of the spinal deformity; the device may be used to position the user with optimal spine alignment for surgical procedure purposes; the device may be used to position, align, realign, approximate, assess, hold, suspend, compress, extend, cue, inhibit, facilitate, and combinations thereof for the purposes of physical therapy or other medical modalities.

During use of the device according to the embodiment of FIGS. 3-10, the weight of the device may be completely supported by the user, or may be partially or fully supported by cords or stretchable tethers to decrease the vertically oriented, downward force vector created by the weight of the device placed on the user's torso and pelvis.

Figure 13:
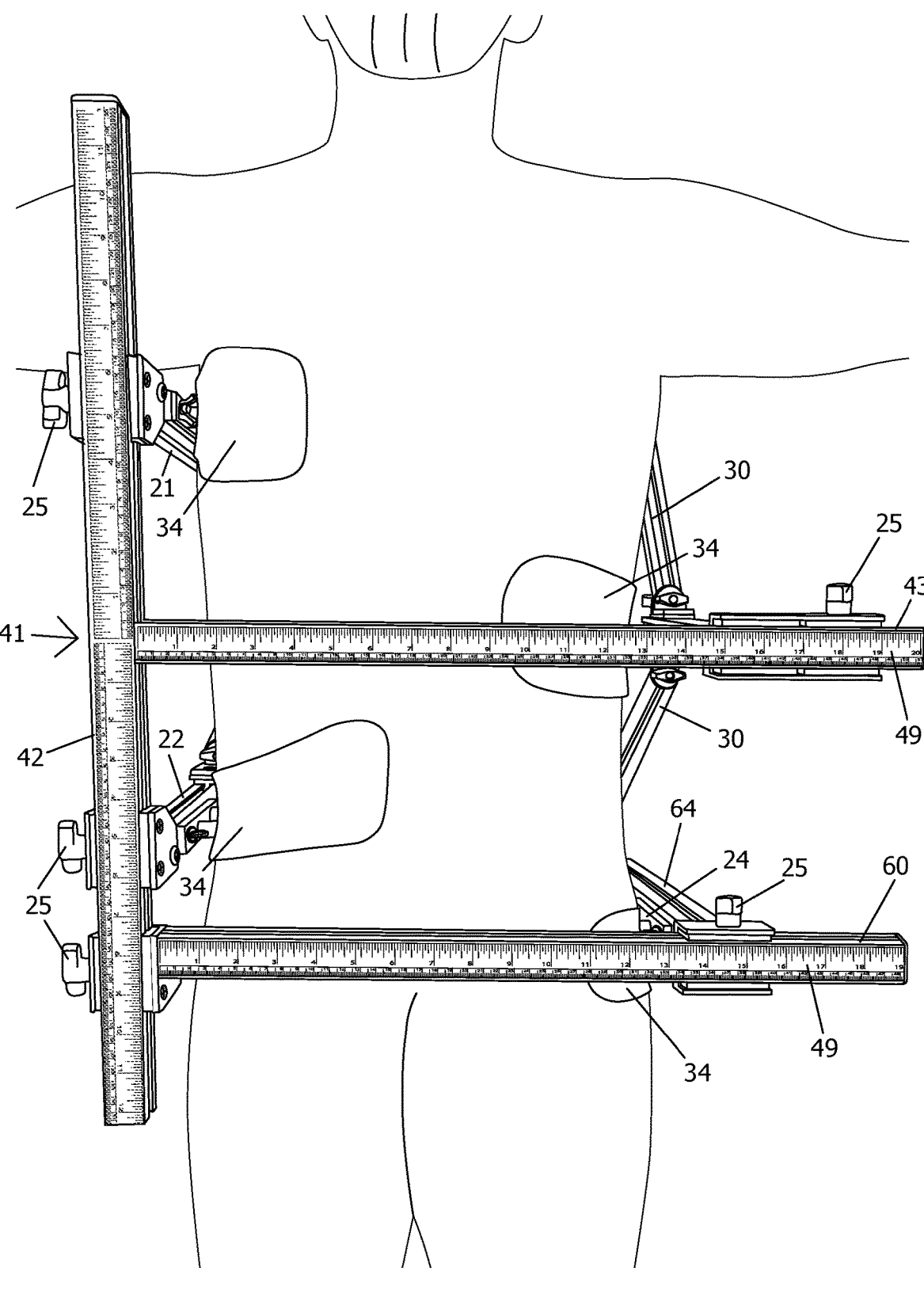
FIG. 13 is a rear view of an embodiment of an orthopedic device with a sliding perpendicular frame member and fourth primary extension positioned on a user with the device oriented and configured for alignment of a double scoliosis curve with a right thoracic apex and a left lumbar apex.

Description of Embodiment of FIG. 13

The description of the embodiment of FIG. 13 is inclusive of description of the embodiment of FIGS. 3-10, heretofore described, and the embodiment of FIG. 13 further comprises a sliding perpendicular frame member 60 that is slidably coupled to the parallel frame member 42. The position of the sliding perpendicular frame member 60 is adjustable vertically, and lockable on the parallel frame member 42 via a thumb screw 25.

A fourth primary extension 64 having a first end and a second end is slidably coupled by its second end to the sliding perpendicular frame member 60. The fourth primary extension 64 possesses at least three slotted surfaces, the slots running parallel to the long axis of the fourth primary extension 64. The slots of the fourth primary extension are configured to accommodate adjustable arms 30, heretofore described. The fourth primary extension 64 is configured to lock in an unlimited number of positions along the length of the sliding perpendicular frame member 60 via a thumb screw 25.

A linear scale 49 is placed or engraven on the posterior surface of the sliding perpendicular frame member 60, and may also be placed or engraven on a lateral surface of the fourth primary extension 64. The linear scale 49 allows for measuring the distances between contact panels 34 in the frontal plane, allows for measuring the distance between contact panels 36 in the sagittal plane, and/or allows for measuring a change in dimensions of the user's torso between the user's torso at rest and in a corrected position.

In the embodiment of FIG. 13 a sliding fixture 24 is disposed on at least one side of the fourth primary extension 64. The position of the sliding fixture 24 is adjustable along the length of the slots of the fourth primary extension 64 running parallel to the long axis of the fourth primary extension 64. Additionally, the sliding fixture 24 is configured to lock in a selected position along the length of the fourth primary extension 64.

In the embodiment of FIG. 13 a contact panel 34 is configured to fasten to the sliding fixture 24 of the fourth primary extension 64. The contact panel 34 of the fourth primary extension 64 comprises a semi-rigid to rigid panel contoured to accommodate the shape of the region of the user's body to which it is intended to contact such that forces are distributed substantially evenly. While the embodiment of FIG. 13 depicts spacers 40 being positioned between the contact panel 34 and sliding fixture 24 of the fourth primary extension, other means for fastening the contact panel 34 to the sliding fixture 24 may be used.

Operation of the Embodiment of FIG. 13

The embodiment of FIG. 13 operates in a manner similar to that of the embodiment of FIGS. 3-10 with additional steps in its operation. The operation of the embodiment of FIG. 13 requires the following steps in addition to that which is heretofore spelled out in the operation of FIGS. 3-10:

After a contact panel 34 has been fastened to each of the first, second, and third primary extensions 21,22,23, a contact panel 34 is fastened to the fourth primary extension 64 via a sliding fixture 24.

During the process of positioning the primary extensions 21,22,23 to the predetermined heights relative to the users body, the sliding perpendicular frame member 60 and fourth primary extension 64 are positioned to the desired height for maximizing improved spine alignment and the sliding perpendicular frame member 60 is locked in its location on the parallel frame member 42 via a thumb screw 25.

After the third primary extension 23 is adjusted medially on the perpendicular frame member 43 so that the corresponding contact panel 34 contacts the intended location on the user's torso and is locked, the fourth primary extension 64 is adjusted medially on the sliding perpendicular frame member 60 so that the contact panel 34 of the fourth primary extension 64 contacts the intended location on the user's torso. Sufficient manual force may be provided to move the contact panel 34 of the fourth primary extension 64 toward the user's body to achieve the desired spinal alignment correction. Then the position of the fourth primary extension 64 on the sliding perpendicular frame member 60 is locked via a thumb screw 25.

Figure 14:
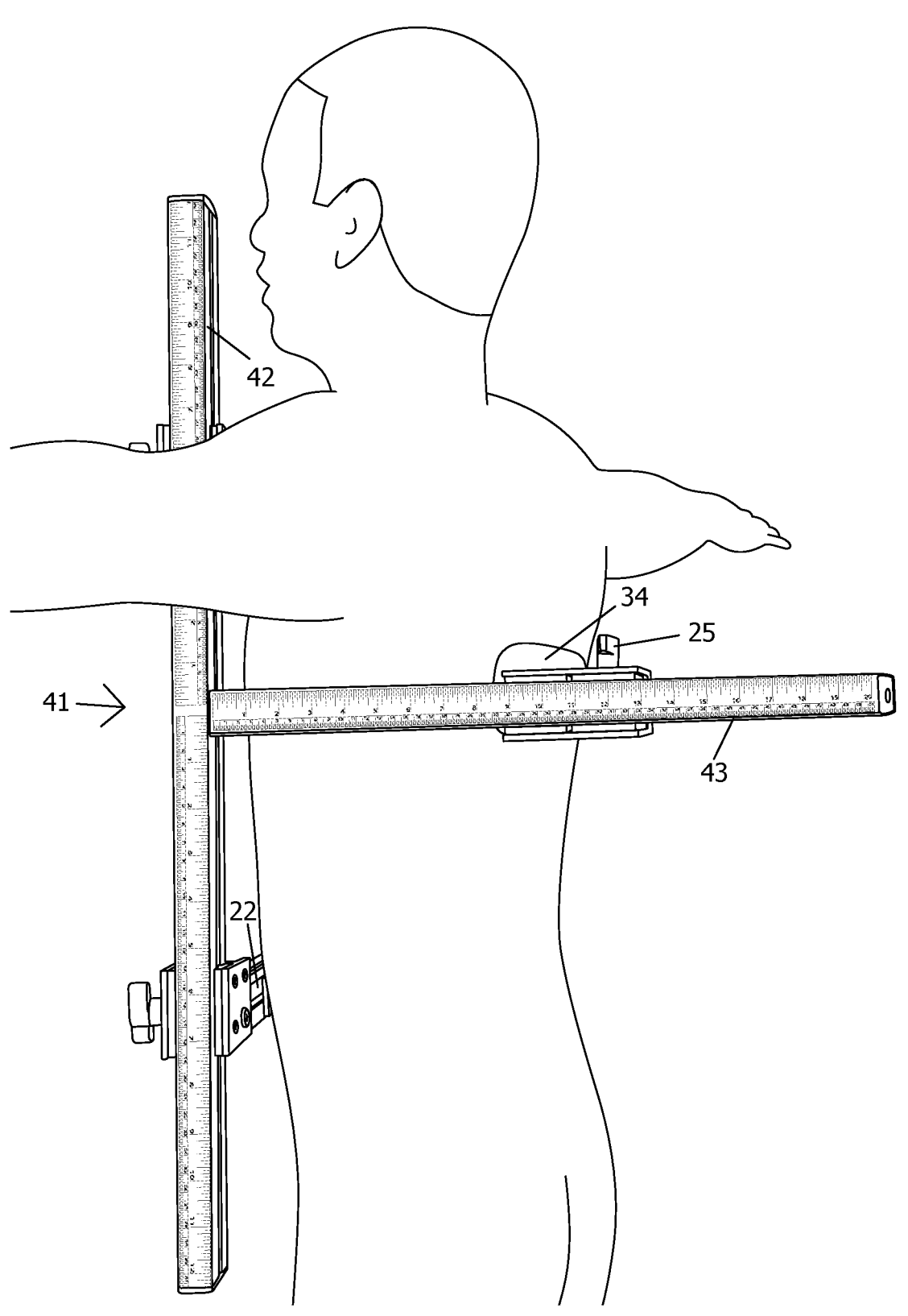
FIG. 14 is a left perspective view of an embodiment of an orthopedic device configured for alignment of hyperkyphosis of the thoracic spine, oriented and configured for contact panels to be applied at the upper anterior pelvis, the superior sternum and the mid thoracic spine region.

Description of embodiment of FIG. 14.

FIG. 14 depicts an adjustment to the orthopedic device relative to the embodiment of the orthopedic device in FIGS. 3-10 wherein the embodiment of FIG. 14 is depicted as not comprising a parallel extender assembly 50. The embodiment of FIG. 14 comprises a sliding fixture 24 disposed on at least one surface of the third primary extension 23. A contact panel 34 is fastened to the sliding fixture 24 of the third primary extension 23.

The embodiment of FIG. 14 is depicted as not comprising adjustable arms 30. While the embodiment of FIG. 14 does not comprise adjustable arms 30, the primary extensions are configured to accept and employ adjustable arm(s) 30.

Operation of Embodiment of FIG. 14

The embodiment of FIG. 14 is configured to move a user's torso into a position in which the user's misaligned spine is closer to that of a physiologically normal spine by the change in position of the contact panels 34, and the effect thereof on user's body and spine position.

The first step in operating the embodiment of FIG. 14 is to fasten a contact panel 34 to each of the first, second and third primary extensions 21,22,23 via sliding fixtures 24, the contact panels 34 being contoured to accommodate the user's body at the intended location of application.

For the purposes of aligning a user's hyperkyphotic spine, the frame assembly 41 may be positioned either to the user's right or left, oriented in such a manner that the first and second primary extensions 21,22 are anterior to the user's torso and the third primary extension 23 is posterior to the user's torso. The embodiment of FIG. 14 depicts the frame assembly 41 as being positioned to the left of the user's torso oriented such that the first primary extension 21 is superior to the second primary extension 22.

After the frame assembly is positioned and oriented appropriately with the first and second primary extension 21,22 anterior to the user, and third primary extension 23 posterior to the user, the position of the device according to the embodiment of FIG. 14 is adjusted so that the contact panel 34 of the third primary extension 23 contacts the posterior midline of the users back directly posterior to the spinous process of the most posterior thoracic vertebrae.

Then, the relative height of the first primary extension 21 is adjusted on the parallel frame member 42 so that the contact panel 34 of the first primary extension 21 is over the desired location on the user's body, which may vary on a case by case basis with a common location of placement being the superior sternum just below the sternal notch.

Then, the relative height of the second primary extension 22 is adjusted on the parallel frame member 42 so that the contact panel 34 of the second primary extension 22 is over the desired location on the user's body which may vary on a case by case basis, with common placement locations including the pubis or abdomen.

Next, the user actively extends his or her torso towards a position in which his or her spine is aligned as close to that of a physiologically normal spine as possible. Additional manual force may be temporarily applied to the user's body to assist in attaining an optimal position. The user's upper extremities may also be temporarily supported on a stable platform to augment thoracic primary extension. In order to assist the user in extending their spine, the device according to FIG. 14 may also be temporary stabilized or leaned against a stable object so that the user may lean into and extend over the contact panel 34 of the third primary extension 23 assisting in alignment of the thoracic spine toward that of a physiologically normal spine.

Finally, with the user maintaining the position of improved spine alignment, the position of the third primary extension 23 is adjusted on the perpendicular frame member 43 by moving it as close to the first end of the perpendicular frame member 43 as the user's body will allow. The position of the third primary extension 23 on the perpendicular frame member 43 is then locked by tightening the thumb screw 25, and the user returns to standing unsupported by stabilized objects.

Goals that can be achieved through application of the device according to the embodiment of FIG. 14 include but are not limited to: a digital optical 3D scan can be performed of the user with the device applied in order to fabricate an orthopedic brace for treatment of the spinal deformity; a radiograph of the user's spine can be conducted with the device applied to determine if the patient's spine possesses sufficient flexibility for an orthopedic brace to effectively align the user's spine; a plaster cast may be applied prior to application of the device and the device and cast removed once the plaster begins to harden to use the plaster cast in fabrication of an orthopedic brace for treatment of the spinal deformity; a plaster cast may be applied prior to application of the device for the purposes of serial plaster casting treatment and the device removed once the plaster has hardened; the orthopedic device according to FIG. 14 may be directly used to brace a user in treatment of the spinal deformity; the device may be used to position the user with optimal spine alignment for surgical procedure purposes.

During use of the device according to the embodiment of FIG. 14, the weight of the device may be completely supported by the user, or may be partially or fully supported by elastic cords or stretchable tethers to decrease the vertically oriented, downward force vector created by the weight of the device placed on the user's torso and pelvis.

Figure 15:
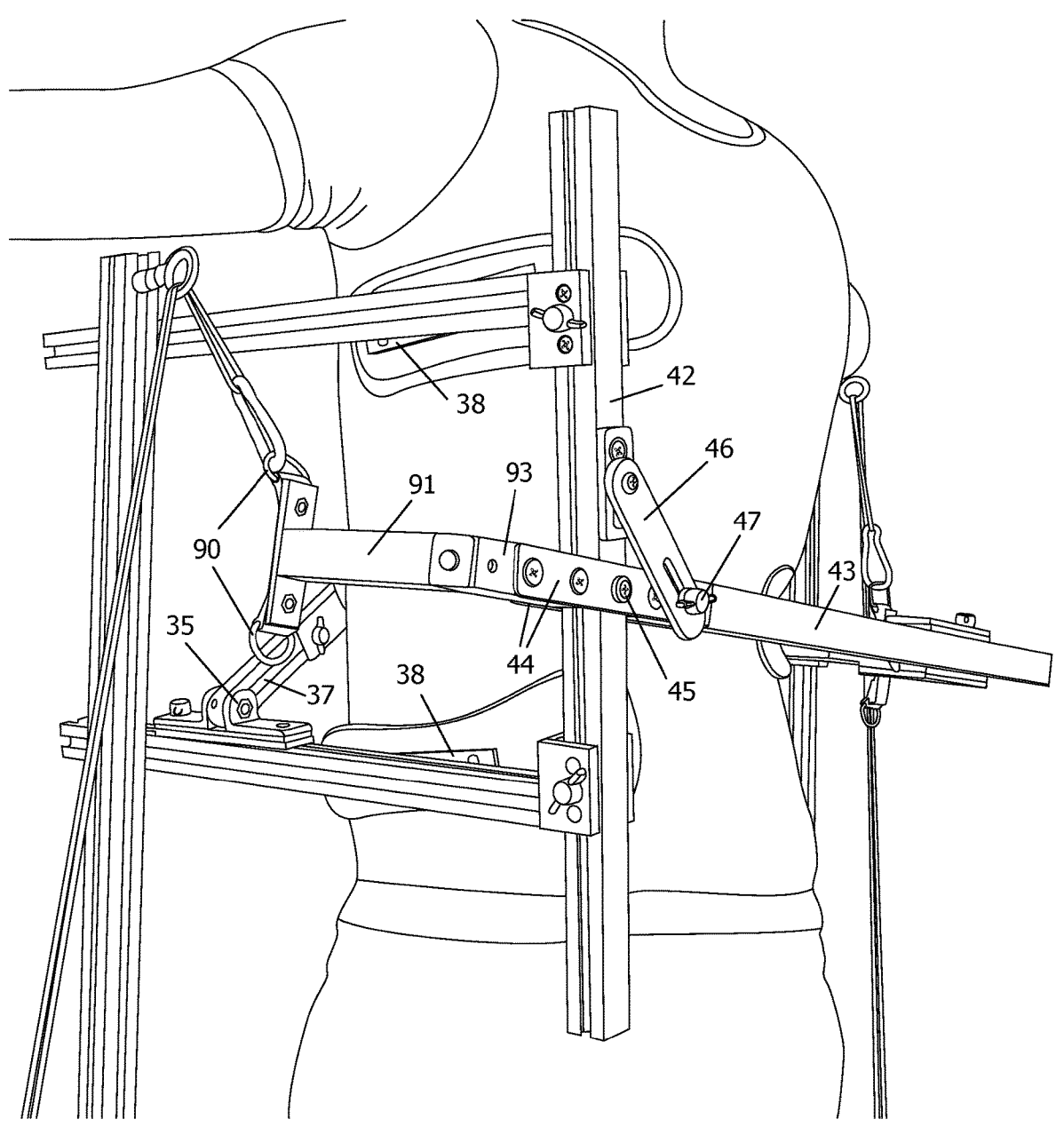
FIG. 15 is a left rear perspective view of an embodiment of the orthopedic device configured with frame brackets, a bracket connector, suspension frame members, suspension loops, and pivoting plates, wherein, the parallel frame member rotates relative to the perpendicular frame member.
Figure 16:
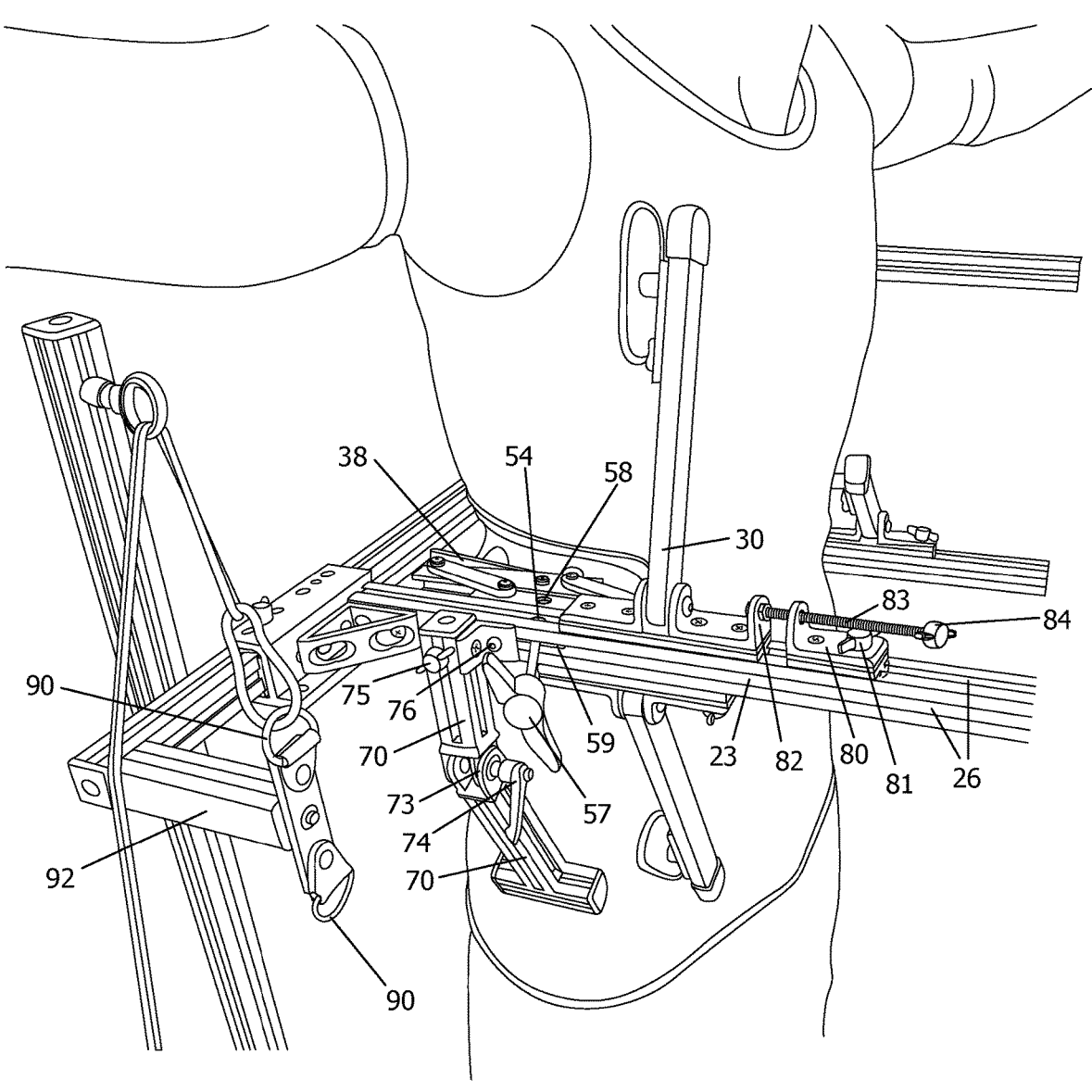
FIG. 16 is a right front perspective view of the orthopedic device of FIG. 15 providing a view of a secondary extension, an anchor of the adjustment arm, a parallel extender assembly, and a second suspension frame member.
Figure 17:
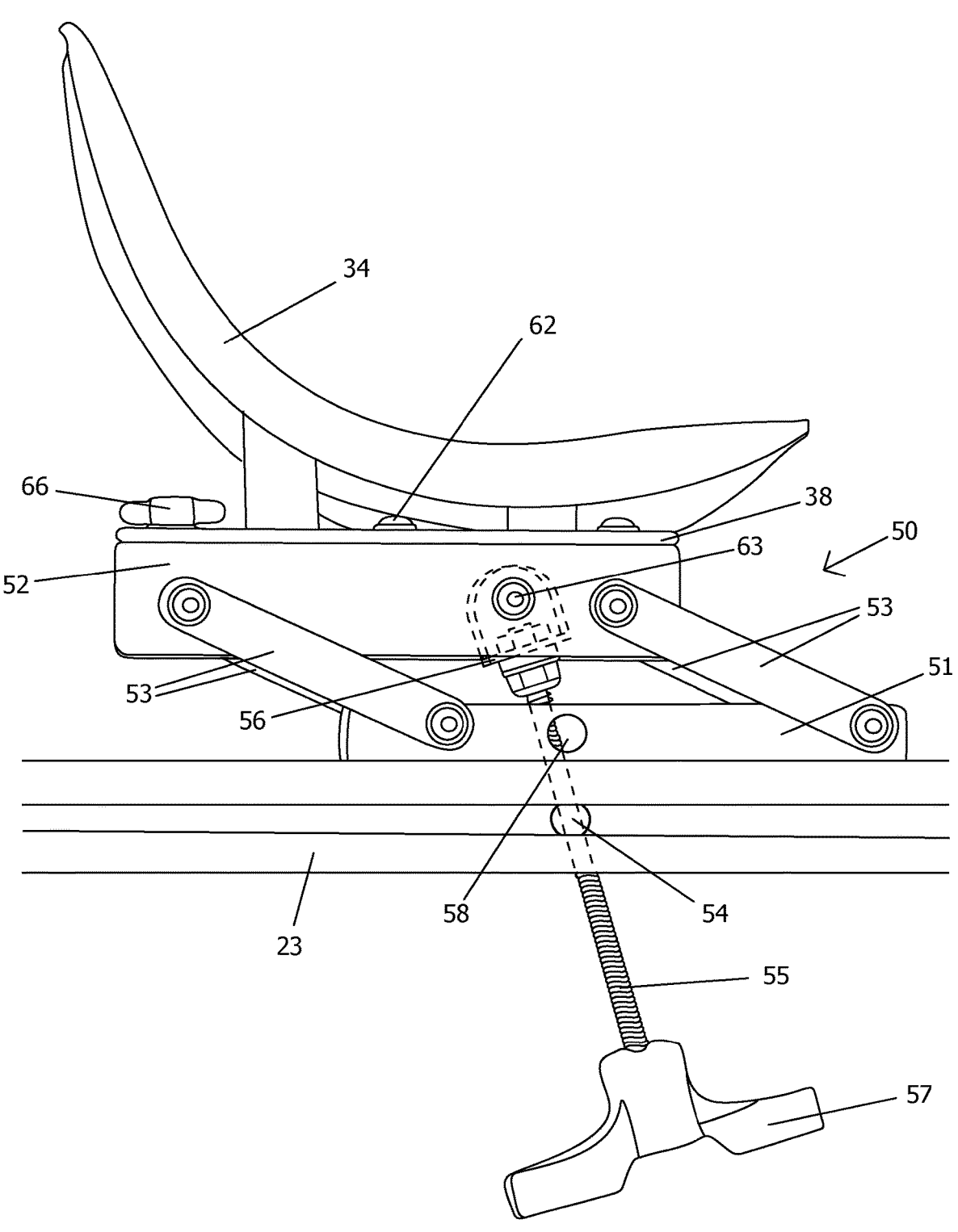
FIG. 17 is a detailed top perspective view of the parallel extender assembly of the embodiment of FIG. 15 showing a pivoting plate, a pivoting shaft bracket, and an adjustment shaft knob.

Description of embodiment of FIGS. 15-17.

FIGS. 15-17 depict an adjustment to the orthopedic device relative to the embodiment of FIGS. 3-10 wherein two frame brackets 44, each having a first end and second end, are connected by the second ends thereof to the first end of the perpendicular frame member 43. The frame brackets 44 are positioned on opposing sides of the perpendicular frame member 43 such that the frame brackets 44 extend past the first end of the perpendicular frame member 43, and extend past the parallel frame member 42 on opposing sides of the parallel frame member 42. Each of the frame brackets 44 define a hole 45, the axis of the hole 45 of each frame bracket 44 aligning with the hole of the other frame bracket 44. The parallel frame member 42 defines a hole located substantially on the centerline of the parallel frame member 42. The hole of the parallel frame member is aligned with the holes 45 of each of the two frame brackets 44. A bolt 45 fits through the holes 45 of the two frame brackets 44, and the parallel frame member 42 with the parallel frame member 42 positioned between the two frame brackets 44. The long axis of the bolt 45 is the axis of rotation around which the parallel frame member 42 rotates relative to the perpendicular frame member 43. The axis of rotation of the parallel frame 42 member is substantially parallel to each of the three primary extensions 21,22,23.

In contrast to the embodiment of FIGS. 3-10, the parallel frame member in the embodiment of FIGS. 15-17 is spaced apart from the perpendicular frame member 43 adequate for the parallel frame member 42 to rotate about the axis of rotation thereof without interference from the perpendicular frame member 43.

In the embodiment of FIGS. 15-17, the first ends of each of the two frame brackets 44 extend past the parallel frame member 42 and connect to a bracket connector 93. The bracket connector 93 has a first end and a second, each of the two frame brackets 44 extending on opposing sides of the second end of the bracket connector 93. The bracket connector 93 is positioned parallel to, and in-line with, the perpendicular frame member 42. The position of the bracket connector 93 is spaced apart from the parallel frame member 42 adequate for the parallel frame member 42 to rotate about the axis of rotation thereof without interference from the bracket connector 93.

In the embodiment of FIGS. 15-17, a stabilizing link 46 having a first end and a second end is pivotally coupled by the first end thereof via a machine screw to the parallel frame member 42 at a location between the first end of the parallel frame member 42 and the point at which the frame bracket 44 connects to the parallel frame member 42. The second end of the stabilizing link 46 slidably and pivotally couples to the perpendicular frame member via a thumb screw 47. The second end of the stabilizing link 46 defines a slot through which the thumb screw 47 fits and fastens to the perpendicular frame member 43 through a corresponding hole in the frame bracket 44.

The embodiment of FIGS. 15-17 depicts another adjustment to the orthopedic device relative to the embodiment of FIGS. 3-10, wherein a first suspension frame member 91 is rigidly connected to the first end of the bracket connector 93, the first suspension frame member 91 being oriented parallel to that of the primary extensions 21,22,23. The first suspension frame member 91 has a first end and a second end, the second end thereof being connected to the first end of the bracket connector 93. Two suspension loops 90 are mounted to the first end of the first suspension frame member 91.

In the embodiment of FIGS. 15-17, a second suspension frame member 92 is rigidly connected to the second end of the perpendicular frame member 43, the second suspension frame member being oriented parallel to that of the primary extensions 21,22,23. The second suspension frame member 92 has a first end and a second end, the second end thereof being connected to the second end of the perpendicular frame member 43. Two suspension loops 90 are mounted to the first end of the first suspension frame member 91.

The suspension loops 90 of both the first and second suspension frame members 91,92 are configured to be connected to by a separate supporting structure wherein the supporting structure supports the weight of the orthopedic device according to the embodiment of FIGS. 15-17 via the suspension loops 90.

The embodiment of FIGS. 15-17 depict another adjustment to the orthopedic device relative to the embodiment of FIGS. 3-10 wherein at least one pivoting plate 38 pivotally mounts to the panel side 28 of at least one of the sliding fixtures 24. The pivoting plate defines a hole through which a machine screw 39 fits that pivotally mounts the pivoting plate 38 to the sliding fixture 24. The pivoting plate 38 rotates around the machine screw 39, and the angle of the pivoting plate 38 relative to the sliding fixture 24 is selectively lockable via the thumb screw 33 of the sliding fixture 24. The contact panel 34 mounts to the pivoting plate 38 via press-fit nuts 48 secured to the pivoting plate 38.

Figure 18:
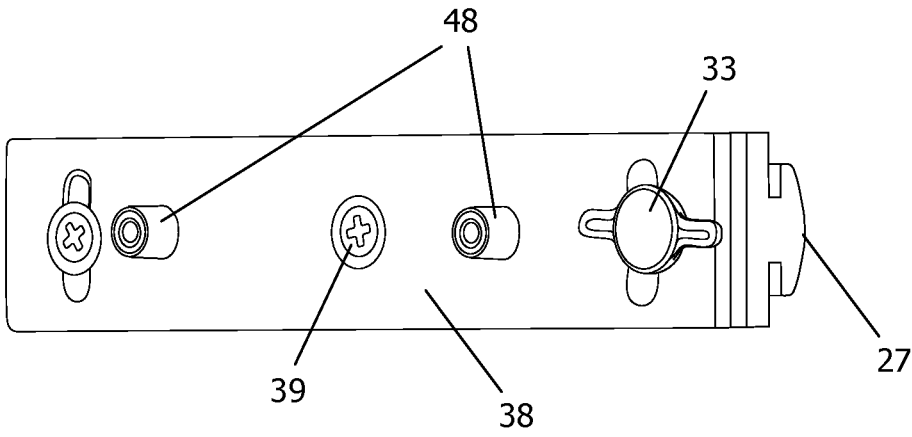
FIG. 18 is a detailed perspective view of the pivoting plate mounted on a sliding fixture of the embodiment of FIG. 15.
Figure 19:
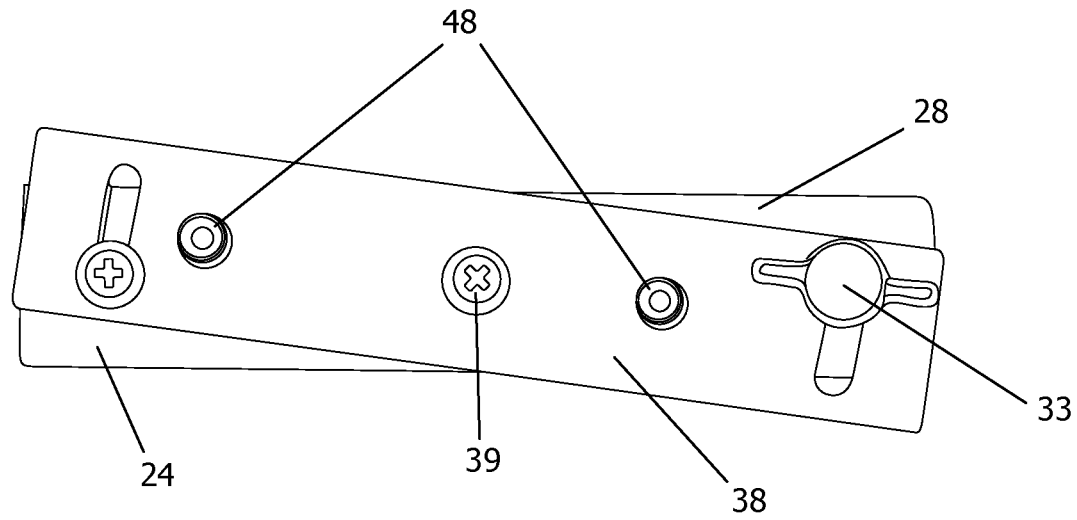
FIG. 19 is a detailed perspective view of the pivoting plate mounted in an angled position on the sliding fixture of the embodiment of FIG. 15.

FIGS. 18-19 provide a detailed view of the pivoting plate 38 of the embodiment of FIGS. 15-17. The pivoting plate 38 is pivotally mounted to the sliding fixture 24.

The embodiment of FIGS. 15-17 depict another adjustment to the orthopedic device relative to the embodiment of FIGS. 3-10 wherein a secondary extension 70 having an elongate body, and having a mount end and a pad end is configured to removably mount at any point along any of the slots 26 defined by the first, second, or third primary extensions 21,22,23. The secondary extension 70 removably mounts to the slot 26 defined by the primary extension toward the mount end of the secondary extension 70, via a thumb screw 75 placed through a hole defined by the secondary extension 70. An anti-rotation mechanism comprising a torsion pin 76 extends through a hole in a flange of the secondary extension 70, the torsion pin 76 configured to fit in the slot 26 defined by the primary extension 23 to which the secondary extension is attached. The torsion pin 76 is configured to prevent rotation of the secondary extension 70 about the thumb screw 75 of the secondary extension 70.

The elongate body of the secondary extension 70 defines a pivoting joint 73 on which the pad end of the at least one secondary extension 70 rotates relative to the mount end of the at least one secondary extension 70, the axis of rotation being substantially parallel to long axis of the primary extension 21,22,23 on which the at least one secondary extension 70 removably mounts. The pivoting joint 73 of the at least one secondary extension 70 is configured to selectively lock the angle of the pad end of the secondary extension relative to the mount end of the secondary extension 70 via a locking knob 74.

The embodiment of FIGS. 15-17 depicts another adjustment to the orthopedic device relative to the embodiment of FIGS. 3-10, wherein an anchor 80 is configured to slideably mount to any one of the slots 26 defined by the first, second, or third primary extensions 21, 22, 23. The anchor 80 is configured to selectively lock at any point along any one of the slots 26 defined by the first, second, or third primary extensions 21,22,23 via a thumb screw 81 placed through a hole defined by the anchor 80. The anchor 80 defines a threaded hole, the threads thereof being configured to match the external threads of an anchor adjustment shaft 83. The anchor adjustment shaft 83 has a first end and a second end.

In the embodiment of FIGS. 15-17, the mount end of at least one adjustable arm is configured with flange 82, the flange defining a hole. The centerline of the hole defined by the flange 82 of the adjustable arm 30 is parallel to the long axis of the primary extension to which the adjustable arm 30 is mounted. The first end of the anchor adjustment shaft 83 extends through the hole of the flange 82 of the adjustable arm 30. The second end of the anchor adjustment shaft 83 extends through the threaded hole of the anchor 80. The anchor adjustment shaft 83 is rotatably coupled to the adjustable arm flange 82 toward the first end of the anchor adjustment shaft via two lock nuts mounted on the anchor adjustment shaft 83 on opposing sides of the adjustable arm flange 82. A knob 84 is mounted on the second end of the anchor adjustment shaft 83.

The embodiment of FIGS. 15-17 depicts another adjustment to the orthopedic device relative to the embodiment of FIGS. 3-10, wherein the parallel extender assembly further comprises a pivoting plate 38, a pivoting shaft bracket 56, an adjustment shaft knob 57, and a hole 58 defined by the stationary plate 51 in which the adjustment shaft engager 54 is configured to fit.

The pivoting plate defines a hole through which a machine screw 62 extends, the machine screw 62 connecting to the moving plate 52. The pivoting plate 38 rotates around the machine screw 62, and the angle of the pivoting plate 38 relative to the moving plate 52 is selectively lockable via the thumb screw 66. The contact panel 34 mounts to the pivoting plate 38 via press-fit nuts 48 secured to the pivoting plate 38.

The pivoting shaft bracket 56 comprising two sides and a base is configured to pivotally mount to the moving plate 52. The moving plate 52 comprises two legs between which the pivoting shaft bracket 56 is located. Each leg of the moving plate 52 defines a hole and each side of the pivoting shaft bracket 56 defines a hole. A pin 63 extends through both holes of the moving plate 52 thereof, and through both holes of the pivoting shaft bracket 56 thereof. The pivoting shaft bracket 56 rotates about the pin 63 thereof relative to the moving plate 52. The second end of the adjustment shaft 55 is rotatably coupled to the pivoting shaft bracket 56 via a hole defined by the base of the pivoting shaft bracket 56. The second end of the adjustment shaft 55 extends through the hole defined by the base of the pivoting shaft bracket 56 and two lock nuts connect to adjustment shaft 55 on opposing sides of the base of the pivoting shaft bracket 56. The adjustment shaft knob 57 is connected to the first end of the adjustment shaft 55.

FIG. 17 provides a detailed view of the parallel extender assembly of the embodiment of FIGS. 15-17. The hole 58 defined by the stationary plate 51 is an alternate location at which the adjustment shaft engager 54 may rotatably fit.

Operation of the Embodiment of FIGS. 15-17

The embodiment of FIGS. 15-17 operates in a manner similar to that of the embodiment of FIGS. 3-10 with an adjustment to steps in its operation. The angle of the parallel frame member 42 is adjusted to the desired angle relative to the perpendicular frame member 43 in order to adjust the coordinates of the first and second primary extension 21,22 relative to the user. The stabilizing link thumbscrew 47 is loosened prior to the aforementioned angle adjustment, and tightened after the aforementioned angle adjustment. This adjustment of the angle of the parallel frame member 42 may be performed prior to adjusting the position of the third primary extension 23 medially on the perpendicular frame member 43.

The angle of at least one pivoting plate 38 is adjusted relative to the sliding fixture 24 and/or moving plate 52 to which the pivoting plate is pivotally mounted. This is performed to accommodate and/or match the rib angle of the user. This is accomplished by loosening the thumbscrew 33, 66, rotating the pivoting plate 38 to the desired angle relative to the sliding fixture 24 and/or moving plate 52 and tightening the thumbscrew 33,66. This adjustment is performed after the orientation of the frame assembly 41, and position of the primary extensions 21,22,23 have been determined, but before positioning the embodiment of FIGS. 15-17 on the patient.

The secondary extension 70 is mounted to the desired primary extension 21,22,23 via the secondary extension thumb screw 75 in order to facilitate a balanced position of the patient in the frontal plane with the embodiment of FIG. 15-17 applied. This is performed when the alignment of the T1 vertebrae of the user is not aligned vertically over the middle of the sacrum of the user in the frontal plane. To apply the secondary extension 70 the mount end of the secondary extension is connected to the desired primary extension 21,22,23 by tightening the thumbscrew 75 with the thumbscrew 75 extending through a threaded nut in a slot of the primary extension 21,22,23. Then the secondary extension pivoting joint knob 74 is loosened with the user holding a position of frontal plane alignment and the pad end of the secondary extension 70 is put into contact with the user's body at the height of the pelvis or below. Then the secondary extension pivoting joint knob 74 is tightened.

The anchor 80 is operated for the purpose of incrementally adjusting the anterior to posterior position of the adjustable arm 30. This is performed by moving the anchor 80 and adjustable arm 30 in tandem with the anchor adjustment shaft 83 connecting the anchor 80 and the adjustable arm 30. Once the adjustable arm 30 has reached the initial desired position, the anchor thumb screw 81 is tightened. The position of the adjustable arm 30 on the primary extension 21,22,23 to which it is mounted is then further adjusted by turning the anchor adjustment shaft knob 84.

What is claimed is:

1. An orthopedic device comprising:
a frame assembly comprising a parallel frame member and a perpendicular frame member, each of the parallel frame member and the perpendicular frame member being substantially elongate in shape, and each having a first end and a second end, the parallel frame member being oriented substantially parallel to a vertical axis of a user when in use, the perpendicular frame member being oriented substantially perpendicular to the vertical axis of the user when in use;
at least three primary extensions each having a mount end and a free end;
wherein the perpendicular frame member is coupled by the first end thereof to the parallel frame member along the length of the parallel frame member between the first end and the second end thereof;
wherein a first of the at least three primary extensions is adjustably disposed by the mount end thereof directly along the length of the parallel frame member between the first end of the parallel frame member and the location at which the parallel frame member is coupled to the perpendicular frame member, the first of the at least three primary extensions having no freedom of translational motion in any direction except translational motion parallel to a long axis of the parallel frame member when the device is in use;
wherein a second of the at least three primary extensions is adjustably disposed by the mount end thereof directly along the length of the parallel frame member between the second end of the parallel frame member and the location at which the parallel frame member is coupled to the perpendicular frame member, the second of the at least three primary extensions having no freedom of translational motion in any direction except translational motion parallel to the long axis of the parallel frame member when the device is in use;
wherein a third of the at least three primary extensions is adjustably disposed by the mount end thereof along the length of the perpendicular frame member between the second end of the perpendicular frame member and the location at which the perpendicular frame member is coupled to the parallel frame member;
further comprising at least one frame bracket belonging to the frame assembly, the at least one frame bracket defining a pivot point, and having a first end, and a second end;
wherein the second end of the at least one frame bracket is connected to the first end of the perpendicular frame member;
wherein the parallel frame member is rotatably coupled to the at least one frame bracket at the pivot point defined by the at least one frame bracket;
wherein the parallel frame member is rotatable about one axis of rotation, the axis of rotation thereof being substantially perpendicular to both the long axis of the parallel frame member and the long axis of the perpendicular frame member;
further comprising a stabilizing link having a first end and a second end;
wherein the stabilizing link is configured to pivotally and slidably couple from the second end thereof to the perpendicular frame member;
wherein the stabilizing link is configured to pivotally couple from the first end thereof to the parallel frame member:
wherein the stabilizing link is adjustably lockable on the frame assembly thereby selectively locking the angle between the parallel frame member and the perpendicular frame member:
wherein the positions of the at least three primary extensions are adjustable along the length of the portion of the frame assembly on which they are disposed;
wherein the at least three primary extensions are substantially parallel to one another.

2. The orthopedic device of claim 1 wherein the parallel frame member and the perpendicular frame member are configured to receive the at least three primary extensions via slots oriented parallel to the long axes of the respective frame members, the mount end of each of the at least three primary extensions being configured to slide and selectively lock in position along the frame member to which they are disposed.

3. The orthopedic device of claim 2 further comprising at least one adjustable arm having a mount end and a free end, the at least one adjustable arm configured to be adjustably disposed on at least one of the at least three primary extensions.

4. The orthopedic device of claim 3, further comprising at least one parallel extender assembly, the parallel extender assembly comprising:
a stationary plate configured to adjustably mount to a primary extension;
at least one strut having a first end and a second end, the first end being coupled to the stationary plate;
a moving plate coupled to the second end of the at least one strut;
an adjustment shaft having a first end and a second end, the second end being coupled to the moving plate,
an adjustment shaft engager coupled to at least one of the stationary plate or the primary extension to which the at least one parallel extender assembly is coupled, the adjustment shaft engager being configured to control the position of the adjustment shaft relative to the component to which the adjustment shaft engager is coupled;

wherein each of the at least one parallel extender assembly is adjustably mounted to a primary extension.

5. The orthopedic device of claim 4, wherein:

each of the at least three primary extensions define at least one slot oriented parallel to the long axis thereof;

the mount end of the at least one adjustable arm is configured to slidably mount in the at least one slot of the at least three primary extensions and selectively lock in position along the length of the at least one slot;

the at least one adjustable arm defines a pivoting joint on which the free end of the at least one adjustable arm rotates relative to the mount end of the at least one adjustable arm, the axis of rotation being substantially parallel to long axis of the primary extension on which the at least one adjustable arm slidably mounts;

the pivoting joint of the at least one adjustable arm is configured to selectively lock the angle of the free end of the adjustable arm relative to the mount end of the adjustable arm.

6. The orthopedic device of claim 5, further comprising at least one sliding fixture having a first end and a second end, and having a projection side and a panel side, wherein the projection side of the sliding fixture is configured to slideably mount to and selectively lock in-place on the at least one slot defined by any one of the at least three primary extensions;

further comprising at least one contact panel, each of the at least one contact panel configured with a contour to accommodate the surface anatomy of the region to which the contact panel is applied;

wherein the at least one contact panel is configured to mount on the at least one sliding fixture.

7. The orthopedic device of claim 6, wherein:

the at least one adjustable arm defines at least one slot oriented parallel to the long axis thereof;

the slot of the adjustable arm is configured to receive the projection side of the at least one sliding fixture.

8. The orthopedic device of claim 7, wherein:

the at least one strut of the at least one parallel extender assembly are four struts of equal length;

the stationary plate is pivotally coupled to the first end of the four struts, each of the four struts configured to rotate about one axis relative to the stationary plate;

the four struts are pivotally coupled by the second ends thereof to the moving plate;

the locations at which the four struts are pivotally coupled to the stationary plate are equal distances from one another respectively, and in the same arrangement relative to one another, as the locations at which the four struts pivotally couple to the moving plate;

the adjustment shaft is threaded with an external spiral thread, the adjustment shaft having a knob mounted on the first end thereof;

the adjustment shaft engager has a cylindrically shaped body, the adjustment shaft engager having a hole through the body thereof, the hole thereof having an axis that is perpendicular to the axis of the cylindrical shaped body of the adjustment shaft engager, the hole thereof having internal threads to match the external threads of the adjustment shaft;

each of the stationary plate and the primary extension to which the at least one parallel adjuster assembly is mounted are configured with a hole to accept the adjustment shaft engager;

the adjustment shaft engager is rotatably mounted in at least one of the hole placed in the extension to which the at least one parallel extender assembly mounts or the hole placed in the stationary plate;

the adjustment shaft is coupled by the second end thereof to the moving plate via a pivoting shaft bracket configured to pivotally mount to the moving plate, the pivoting shaft bracket being configured to rotatably mount to the second end of the adjustment shaft;

the at least one parallel extender assembly is comprised of at least one material selected from the group of metal, and plastic, and combinations thereof, the selected material being of sufficient rigidity and strength to prevent collapse or fracture of the parallel extender assembly or any components thereof.

9. The orthopedic device of claim 8, further comprising:

a pivoting plate defining a pivot point, the pivoting plate configured to pivotally mount on the panel side of the at least one sliding fixture, the pivoting plate configured to be mounted on by the at least one contact panel;

wherein the at least one contact panel mounts to the sliding fixture via the pivoting plate;

wherein the sliding base defines a pivotal connection point whereto the pivoting plate pivotally connects;

wherein the angle of the pivoting plate relative to the sliding base is selectively lockable.

10. The orthopedic device of claim 9 further comprising:

at least one secondary extension having an elongate body, the secondary extension having a mount end and a pad end, the mount end thereof configured to removably mount to any of the at least one slot of any of the at least three primary extensions at any point along the length thereof;

wherein the elongate body of the secondary extension defines a pivoting joint on which the pad end of the at least one secondary extension rotates relative to the mount end of the at least one secondary extension, the axis of rotation being substantially parallel to long axis of the primary extension on which the at least one secondary extension removably mounts;

the pivoting joint of the at least one secondary extension is configured to selectively lock the angle of the free end of the secondary extension relative to the mount end of the secondary extension;

the pad end of the at least one secondary extension is configured to accommodate the surface anatomy of the region to which the pad end of the at least one secondary extension is applied.

11. The orthopedic device of claim 10 wherein:

the pivoting joint of the at least one secondary extension is configured to selectively lock the angle of the free end of the adjustable arm relative to the mount end of the adjustable arm via a locking knob;

the mount end of the at least one secondary extension defines a hole extending from the grab side to the connecting side;

the mount end of the at least one secondary extension removably mounts to any of the at least three primary extensions via a thumb screw placed through the hole defined by the mount end, the thumb screw fastening to a nut placed into any of the at least one slot of any of the at least three primary extensions;

an anti-rotation mechanism protruding from the secondary extension is configured to fit into the slot to which the at least one secondary extension is connected to prevent rotation of the at least one secondary extension around the thumb screw of the secondary extension.

12. The orthopedic device of claim 11 further comprising:

a linear scale disposed on at least one selected from the group of the perpendicular frame member, the parallel frame member, the three primary frame members, and combinations thereof;

a force plate disposed on at least one selected from the group of the surface of the at least one contact panel configured to face the user, or the surface of the at least one contact panel facing the primary extension to which the contact panel is indirectly connected.

13. The orthopedic device of claim 12 further comprising:

at least one anchor configured to slidably mount to any one of the slots defined by the three primary extensions, the at least one anchor configured to selectively lock at any point along the slots thereof;

wherein the at least one anchor is adjustably connected to the at least one adjustable arm via an anchor adjustment shaft, the anchor adjustment shaft having a substantially elongate body having a first end and a second end, the first end of the anchor adjustment shaft being rotatably coupled to the adjustable arm, the second end of the anchor adjustment shaft being adjustably coupled to the at least one anchor.

14. The orthopedic device of claim 13 further comprising:

a bracket connector having a first end and a second end, the second end connected to the first end of the at least one frame bracket;

a first and a second suspension frame member, each of the first and second suspension frame members having a first end and a second end;

wherein the second end of the first suspension frame member is connected to the first end of the bracket connector;

wherein the second end of the second suspension frame member is connected to the second end of the perpendicular frame member;

further comprising at least two loops;

wherein a first of the at least two loops is disposed on the first end of the first suspension frame member;

wherein a second of the at least two loops is disposed on the first end of the second suspension frame member;

wherein the at least two loops are configured to connect to and be supported by a separate support structure, the weight of the orthopedic device being supported by the at least two loops.

15. The orthopedic device of claim 14 wherein the orthopedic device is configured to at least, measure, position, align, realign, approximate, assess, hold, suspend, compress, extend, cue, inhibit, facilitate, and combinations thereof, a musculoskeletal region of a user, the musculoskeletal region thereof being oriented substantially parallel to the parallel frame member.

16. The orthopedic device of claim 15 wherein the orthopedic device is configured to at least, measure, position, align, realign, approximate, assess, hold, suspend, compress, extend, cue, inhibit, facilitate, and combinations thereof, a human spine.

\* \* \* \* \*